(12) United States Patent
George et al.

(10) Patent No.: US 9,295,760 B2
(45) Date of Patent: Mar. 29, 2016

(54) BLOCK COPOLYMER BLENDS

(75) Inventors: Peter George, Marcoola (AU); Justin John Cooper-White, Upper Brookfield (AU); Tristan Croll, St Lucia (AU)

(73) Assignee: THE UNIVERSITY OF QUEENSLAND, Queensland (AU)

( * ) Notice: Subject to any disclaimer, the term of this patent is extended or adjusted under 35 U.S.C. 154(b) by 770 days.

(21) Appl. No.: 13/263,898

(22) PCT Filed: Apr. 9, 2010

(86) PCT No.: PCT/AU2010/000405
§ 371 (c)(1),
(2), (4) Date: Oct. 11, 2011

(87) PCT Pub. No.: WO2010/115243
PCT Pub. Date: Oct. 14, 2010

(65) Prior Publication Data
US 2012/0034433 A1 Feb. 9, 2012

(30) Foreign Application Priority Data
Apr. 9, 2009 (AU) ................................ 2009901555

(51) Int. Cl.
*C08L 53/00* (2006.01)
*A61L 27/48* (2006.01)
*C08G 65/332* (2006.01)
(Continued)

(52) U.S. Cl.
CPC .............. *A61L 27/48* (2013.01); *C08G 65/3328* (2013.01); *C08G 65/33337* (2013.01); *C08G 65/33358* (2013.01); *C08L 25/06* (2013.01); *C08L 71/02* (2013.01); *C08L 53/00* (2013.01);
(Continued)

(58) Field of Classification Search
CPC ....................................................... C08L 53/00
See application file for complete search history.

(56) References Cited

U.S. PATENT DOCUMENTS 5,728,588 A 3/1998 Caldwell et al.
5,834,583 A 11/1998 Hancock et al.
(Continued)

FOREIGN PATENT DOCUMENTS

WO WO 98/31734 7/1998
WO WO 99/52560 10/1999
(Continued)

OTHER PUBLICATIONS

"Using Self-Assembled Monolayers to Understand the Interactions of Man-Made Surfaces with Proteins and Cells," Mrksich et al., 1996, Annual Reviews of Biophysical and Biomolecular Structures, 25, p. 55-78.*

(Continued)

*Primary Examiner* — Ian Rummel
(74) *Attorney, Agent, or Firm* — Nixon & Vanderhye P.C.

(57) ABSTRACT

A method of producing a structure having a polymer surface with a plurality of surface domains, the surface being formed by the steps of: forming a liquid composition comprising at least one surface polymer, at least one block copolymer and at least one common solvent, the at least one block copolymer having the general formulae A-B-C, wherein A is a polymer which is the same as the surface polymer or fully miscible or partially immiscible with the surface polymer; B is a polymer which is more immiscible in the surface polymer than polymer A; and C is a terminal group; and solidifying the liquid composition to form the structure having the surface with the plurality of surface domains.

13 Claims, 16 Drawing Sheets

(51) Int. Cl.
C08G 65/333 (2006.01)
C08L 25/06 (2006.01)
C08L 71/02 (2006.01)
C08L 87/00 (2006.01)

(52) U.S. Cl.
CPC ........... *C08L 87/005* (2013.01); *C08L 2205/05* (2013.01); *Y10T 428/24802* (2015.01)

(56) References Cited

U.S. PATENT DOCUMENTS

| | | |
|---|---|---|
| 6,444,318 B1 | 9/2002 | Guire et al. |
| 2007/0269480 A1 | 11/2007 | Richard et al. |

FOREIGN PATENT DOCUMENTS

| | | |
|---|---|---|
| WO | WO 02/077159 | 10/2002 |
| WO | WO 2004/037310 | 5/2004 |
| WO | WO 2005/028550 | 3/2005 |

OTHER PUBLICATIONS

International Search Report for PCT/AU2010/000405, mailed May 14, 2010.
Written Opinion of the International Searching Authority for PCT/AU2010/000405, mailed May 14, 2010.

* cited by examiner

BLOCK COPOLYMER BLENDS

This application is the U.S. national phase of International Application No. PCT/AU2010/000405, filed 9 Apr. 2010, which designated the U.S. and claims priority to Australia Application No. 2009901555, filed 9 Apr. 2009, the entire contents of each of which are hereby incorporated by reference.

FIELD OF THE INVENTION

The present invention relates generally to polymer structures having functionalised surface characteristics and to a method for preparing the same. The polymer structures are particularly suitable for use in the field of biomaterials where the attachment of desirable molecules to a surface is required, and it will therefore be convenient to describe the invention with an emphasis toward this application. However, it is to be understood that the polymer structures may be used in various other applications.

BACKGROUND OF THE INVENTION

The working environment for many polymers requires attachment of desirable molecules to the polymer (then acting as a substrate). Particularly in the field of biomaterials, many conventional polymers proposed as biomaterials lack the ability to properly interact with or support biological material, which leads to undesirable biological responses.

It has become recognized that cellular behaviour is determined by the local microenvironment. The cellular microenvironment consists of cell-cell contacts, soluble signalling molecules and an interconnected network of macromolecules known as the extra cellular matrix (ECM), and provides three major categories of physico-chemical signalling; chemical, topographical and mechanical. Chemical signalling from the microenvironment is mediated by membrane proteins (predominantly integrins, but also cadherins, cell adhesion molecules (CAM's) and selectins) that link the cell to the proteins of the ECM and to other cells. Chemical signalling from the ECM is incredibly complex and has been shown to regulate many cellular processes, including proliferation and differentiation. Cells not only respond to the chemical composition of the ECM but also the spatial location of adhesive sites, the surface structure presented to the cell, and the mechanical properties of the matrix.

Whilst many polymeric biomaterials (such as poly(glycolic acid), polylactic acid) and their copolymers, poly(ε-caprolactone), polyurethanes, etc) have been used in an attempt to mimic the ECM, their inherent characteristics, however, limit their suitability for the controlled attachment and subsequent growth of cells and tissues. Their hydrophobic nature, in fact, leads to the adsorption of a non-physiological layer of (mostly denaturated) protein on their surface, further leading to uncontrollable cell-biomaterial interactions and cell responses. It is important in biomaterials applications to eliminate these interactions in favour of tailored biochemical communications with cells via surface-localised peptide or protein signals. It is therefore desirable in many cases to tailor the surfaces of biomaterials to be bioactive, so they can interact favourably with proteins and cells, for instance promoting cell attachment, proliferation, differentiation and ultimately tissue regeneration.

Surface modification is a widely adopted method because it can enhance biofunctionality, tribological properties, and the biocompatibility of a material surface, while keeping the bulk properties intact. In general, the aims of surface modification of biomaterials are to overcome non-specific protein adsorption in vivo, precision immobilization of signalling groups on surfaces, the development of synthetic materials with controlled and tailored properties for drug and cell carriers, biologically inspired materials that mimic natural processes, and the design of sophisticated 3D architectures to produce well-defined patterns for developing bioMEM devices, bioassays, and tissue engineering scaffolds.

Undesirable cellular responses may be controlled by altering the chemical and/or physical properties of the surface of the polymer material. Thus, polymer films can be tailored for specific applications (e.g. tissue engineering) by modification of their surfaces. These techniques include plasma treatments, ion-discharge, surface grafting and wet chemistry methods. Thus, surface modification has become an increasingly popular method of improving biocompatibility and biofunctionality of biomaterials.

While a number of methods exist to functionalise surfaces of polymers (eg those often used in traditional cell culture), many are limited in their capacity to; (i) modify two and three dimensional constructs to an equal extent on all surfaces available to cells; (ii) present multiple bioactive molecules; and (iii) control the spatial location of bioactive molecules. Thus, there is a need to address these limitations.

Reference to any prior art in the specification is not, and should not be taken as, an acknowledgment or any form of suggestion that this prior art forms part of the common general knowledge in Australia or any other jurisdiction or that this prior art could reasonably be expected to be ascertained, understood and regarded as relevant by a person skilled in the art.

SUMMARY OF THE INVENTION

To address, or at least ameliorate, the limitations of the prior art, the applicant has adopted the strategy of utilising block copolymers to functionalise polymer surfaces. Block copolymers consist of alternating segments of two or more chemically distinct polymers. The salient feature of these materials is their ability to self organise into a wide range of micro-phase separated structures generating patterned surfaces that have domain sizes in the order of 10-100 nm. While the invention will be described with reference to surface modification in biological and pharmaceutical applications, the invention is not intended to be restricted to these applications, and polymers of the invention, and those produced by the methods of the invention, may also be used in industrial and non-biological applications.

According to an aspect of the invention, there is provided a method of producing a structure having a polymer surface with a plurality of surface domains, the surface being formed by the steps of:

forming a liquid composition comprising at least one surface polymer, at least one block copolymer and at least one common solvent, the at least one block copolymer having the general formulae A-B-C, wherein A is a polymer which is the same as the surface polymer or fully miscible or partially immiscible with the surface polymer;
B is a polymer which is more immiscible in the surface polymer than polymer A; and
C is a terminal group; and
solidifying the liquid composition to form the structure having the surface with the plurality of surface domains.

The surface polymer is a polymer forming the bulk of the surface of a structure, for instance a scaffold or biomedical device, which may include a coating on the surface of a substrate. Preferably, the surface polymer is a homopolymer.

The C group may be a terminal portion of the B block.

The liquid composition preferably comprises (i) surface polymer in an amount of about 5 wt % of the total solution, and (ii) block copolymer in an amount of up to about 1 wt % of the total solution. The ratio of block copolymer in surface polymer preferably ranges from 1 part in 2 million to where the surface polymer is the block copolymer.

It is preferable that the B-C block of the block copolymer characterise the surface domain, with the A block being substantially embedded in the surface polymer. The terminal group C is generally a small molecule (eg no larger than an oligomer) or moiety which does not substantially affect the miscibility of B in A or the surface polymer. The terminal group C is available for further interaction with objects external to the structure before or after the surface is formed, but preferably after the surface is formed. In this way, the formed surface may be functionalised for any number of applications.

The structure of the present invention may be a stand-alone structure (for instance one having a surface, or a plurality of surfaces having surface domains of B-C, or C).

In accordance with another aspect of the invention, there is provided a polymer structure comprising a surface formed substantially from a surface polymer and having a plurality of functionalised surface domains extending from or formed in the surface of the surface polymer, the functionalised surface domains being formed by solidifying a block copolymer of the general formulae A-B-C, wherein A is a polymer which is the same as the surface polymer or fully miscible or partially immiscible with or substantially miscible in the surface polymer;

B is a polymer which is more immiscible in the surface polymer than polymer A; and C is a terminal group.

In another embodiment, the structure of the present invention may be a coating, film or surface applied to the surface of an existing substrate or support (for instance a tissue scaffold, cell-culture plastic-ware, bioassay platform, microbeads for a suspension culture), and also referred to herein as the substrate surface. Hence in some embodiments of the invention, the solidification process (ie the step of solidifying the liquid composition to form the structure) may be spin casting, dip coating, ink jet printing, contact printing, roll coating or other known form of applying a coating to a support surface. This enables a structure such as a 3-D tissue scaffold to be formed in which the substrate (the tissue scaffold prior to surface modification) provides the physical support structure and the surface coating of the surface polymer and the A-B-C block copolymer on the substrate provides surface domains on the surface which are more readily able to be appropriately modified (eg by a bioactive) for the intended end use.

In this embodiment, the at least one surface polymer and the at least one block copolymer are solidified onto a substrate surface as the structure of the invention. The resulting surface on the substrate is then thus provided with a plurality of surface domains. The block copolymer B block is provided with a terminal group C, which is available for further interaction with objects external to the structure before or after the surface is formed, but preferably after the surface is formed. In this way, the formed surface may be functionalised for any number of applications.

The substrate surface may be any known in the art. Preferably, the substrate surface is compatible with the surface polymer or has been pre-treated to enable or enhance attachment of the surface polymer to the substrate surface. It is not critical that the substrate surface and surface polymer have compatible characteristics. For example a hydrophobic surface polymer may be applied to a substrate surface which is hydrophilic in its normal state by prior treatment of the substrate surface.

In order to reduce the possibility of interaction between B of the block copolymer and the substrate surface, it is preferable that the coating thickness be greater than 25 nm, and preferably greater than 100 nm. Without wishing to be bound by theory, it is believed that the coating thickness should be more than 5 times the radius of gyration of the block copolymer. The typical radius of gyration of the block copolymer used in this invention is 5-20 nm. Hence, the coating thickness should be at least more than 5 nm and in some instances may be more than 100 nm.

It is preferable that the B-C block of the block copolymer characterise the surface domain with the A block embedded in the surface polymer. The surface polymer may be hydrophobic or hydrophilic. A requirement of the block copolymer is that one end of the polymer (section A) is the same polymer type as the surface polymer or is miscible or only partially immiscible in the surface polymer.

If, for example, the surface polymer of a support or a polymer structure, ie the substrate polymer, is hydrophobic, incorporation of a functional B-C block into the block copolymer system which is, for example, hydrophilic, will result in a nano-patterned surface wherein specific locations within the surface (ie those correlating to the C section) can be conjugated to bioactive molecules.

The block copolymer may be an amphiphilic di-block copolymer system A-B that generates a specific surface pattern via programmed phase separation. This A-B system has incorporated, either pre- or post-manufacture, a C terminal group to make an A-B-C polymer, which may be specifically utilised to bind biological molecules. The C terminal group acts as a link or terminal molecule on the A-B system. The C molecule may be a suitable reactive small molecule, moiety or oligomer which does not substantially affect the miscibility of B in A or the surface polymer. The terminal group C is available for further interaction with objects external to the structure before or after the surface is formed, but preferably after the surface is formed. In this way, the formed surface may be functionalised for any number of applications.

By exploiting block copolymer phase separation, and specific reactivity of an incorporated C (terminal group), bioactive molecules may be precisely positioned on a surface with resolution on the 10 nm length scale. This provides the potential to authentically emulate the cellular micro to nano-environment.

Additionally by incorporation of a C terminal group, bioactive molecules or pharmaceutical molecules can be immobilised or fixed to a substrate molecule or surface. By careful selection of the block copolymer, the bio-molecule or pharmaceutical can be cleaved from the support or surface under conditions where the C terminal group of the block copolymer molecule degrades and releases the biomolecule or pharmaceutical.

The invention enables the development of an artificial cell culture system that can modulate cellular behaviour (including stem cells). Such a system can be integrated, as a continuous source of cells, into a plethora of bioreactor systems allowing the generation of products from a well-characterized master cell bank. Such a platform would reduce the cost and improve the safety of cellular therapies. Additionally, it allows the manufacture of a device for the precise manipulation of the designed microenvironment on the nanometer length scale.

In a preferred form, the invention provides an artificial cell culture system and a method of producing an artificial cell culture environment for the precise engineering of cellular micro to nano-environments by controlling the presentation and spatial location of bound biological signals to modulate cellular behaviour (ie direct differentiation of hESC into a desired lineage) whilst preventing non-specific interactions.

Thus, in another aspect of the invention there is provided a method for producing an artificial culture environment comprising the steps of forming a functionalised surface on a substrate surface, the functionalised surface comprising a surface formed substantially from a surface polymer and having a plurality of functionalised surface domains extending from or formed in the surface of the surface polymer, the functionalised surface domains being formed by solidifying onto the substrate surface a block copolymer of the general formulae A-B-C, wherein A is a polymer which is the same as the surface polymer or fully miscible or partially immiscible with or substantially miscible in the surface polymer;

B is a polymer which is more immiscible in the surface polymer than polymer A; and C is a terminal group; and attaching a selected biomolecule to the C block to form the functionalised surface domains.

In this method the selected biomolecule, or molecules that have biofunctionality, may be attached directly to the terminal group C or through the use of a coupled intermediate molecule which is first attached to the terminal group C.

Preferably, the functionalised surface domains are nanoscale and the functionalised surface is nano-patterned.

In an aspect of the invention there is provided an artificial cell culture system comprising a substrate surface coated with a surface polymer including a plurality of functionalised surface domains, the functionalised surface domains being formed of a block copolymer of the general formula A-B; the A block of the block copolymer being embedded in the surface polymer with the B block extending from or formed in the surface polymer; and a selected biomolecule attached to the B block.

In a preferred form of this aspect, A is a polymer which is the same as the surface polymer or fully miscible or partially immiscible with or substantially miscible in the surface polymer and B is a polymer which is more immiscible in the surface polymer than polymer A.

The selected biomolecule, or molecules that have biofunctionality, may be considered the terminal group C.

Preferably, the functionalised surface domains are nanoscale and the surface polymer is nano-patterned.

The invention enables the development of an in vitro bioassay platform that can provide highly specific immobilisation of desired bioactives (e.g. antibodies) and their presentation in required conformations for maximum binding of a second complementary bioactive (e.g. antigens). Such a platform would enhance assay specificity and sensitivity and reduce cost. Additionally, it allows the manufacture of a device for the precise attachment of single bioactives on the nanometer length scale.

In a preferred form, the invention provides a bioassay platform and a method of producing a bioassay surface for the precise engineering of bioactive availability by controlling the presentation and spatial location of bound bioactives to capture complementary bioactives whilst preventing non-specific interactions.

Thus, in another aspect of the invention there is provided a method for producing a bioassay surface comprising the steps of forming a functionalised surface on a substrate surface, the functionalised surface comprising a surface formed substantially from a surface polymer and having a plurality of functionalised surface domains extending from or formed in the surface of the surface polymer, the functionalised surface domains being formed by solidifying onto the substrate surface a block copolymer of the general formulae A-B-C, wherein A is a polymer which is the same as the surface polymer or fully miscible or partially immiscible with or substantially miscible in the surface polymer;

B is a polymer which is more immiscible in the surface polymer than polymer A; and C is a terminal group; and attaching a selected biomolecule to the C block to form the functionalised surface domains.

In this method the selected biomolecule, or molecules that have biofunctionality, may be attached directly to the terminal group C or through the use of a coupled intermediate molecule which is first attached to the terminal group C.

Preferably, the selected biomolecule is one which is complementary to an other molecule of interest for which specific binding to the bioassay surface is desired.

Preferably, the functionalised surface domains are nanoscale and the functionalised surface is nano-patterned.

In a preferred form of the invention, the interaction between the surface polymer and block copolymer results in a phase separation of the block copolymer and surface polymer. The phase separation of block copolymer and surface polymer is controlled by the interaction of polymer segments, size and volume fraction of polymer segments, and chain connectivity, as well as being strongly influenced by interactions with substrate materials and by thickness constraints. The combination of these factors allows for the generation of a number of unique phase separated surface structures that have surface domain sizes preferably in the order of 10-100 nm. Furthermore, the size, spatial location and periodicity of these structures is tunable via altering the volume fraction of block components, the degree of polymerisation and the interaction between components.

Without wishing to be limited by theory, the ability to prepare phase separated surface structures or aggregates of the block copolymer extending from or formed in the surface of the surface polymer is believed to be associated with the interaction of the surface polymer and the block copolymer. Each molecule of surface polymer in the solution is associated with the solvent equally in all directions. Due to the amphiphilic nature of the block copolymer, it has surfactant characteristics driving the formation of micellar aggregates or alternatively adsorption onto a free surface or interface.

Those skilled in the art will appreciate that solvent-polymer interaction parameters and surface energy parameters may also be used as a guide in determining whether a material is likely to function as a solvent or a non-solvent for a given polymer. Thus, high interaction parameters are indicative of non-solvent properties, whereas low interaction parameters are indicative of good solvent properties. Solubility parameters provide an easy numerical method of rapidly predicting the extent of interaction between materials, particularly liquids and polymers. They are useful in ensuring the suitability of polymers for practical applications and in formulating blends of solvents for particular purposes.

As used herein, except where the context requires otherwise, the term "comprise" and variations of the term, such as "comprising", "comprises" and "comprised", are not intended to exclude further additives, components, integers or steps.

BRIEF DESCRIPTION OF THE DRAWINGS

Embodiments of the invention will now be described by way of example with reference to the accompanying drawings in which.

DETAILED DESCRIPTION OF THE EMBODIMENTS

Figure 1:
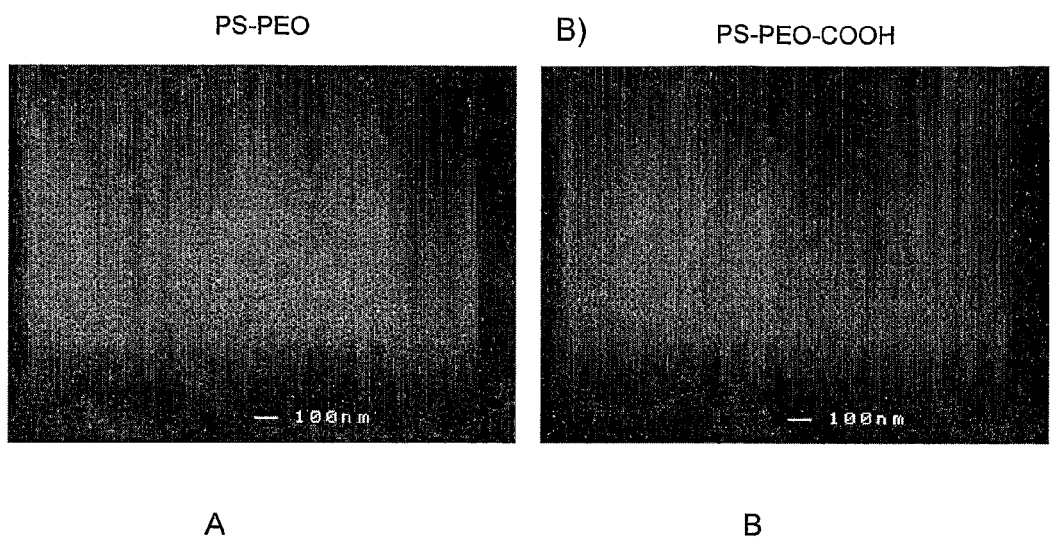
FIG. 1 Scanning electron micrograph of spin cast block copolymer films of a) PS-PEO and b) PS-PEO modified to have a terminal carboxylic acid group.

The invention in its broadest form is a method of producing a polymer structure having a surface with a plurality of functionalised surface domains. The method involves forming a liquid composition comprising at least one surface polymer, at least one block copolymer and at least one common solvent. The block copolymer has the general formulae of A-B-C, where A is a polymer of the same polymer type as the surface polymer or a polymer which is miscible or partially immiscible in the surface polymer; B is a polymer having a higher level of immiscibility to polymer A; and C is a terminal group which is a reactive molecule or oligomer. The skilled person would know which C groups were suitable, examples of which are included in the specification. The method further includes the step of solidifying the at least one block copolymer.

In a preferred form of the invention, the block copolymer is formed having a hydrophilic block and a hydrophobic block. As the surface polymer is preferably hydrophobic, the block copolymer structures will align within the surface polymer such that hydrophilic blocks extend from, or lie within, the surface of the surface polymer. The block copolymer may be formed from more than two monomer or polymer types but it is preferable that the polymer of the surface polymer is present at one end of the block copolymer (ie A block).

The solidification process may be spin casting, dip, coating, ink jet printing, contact printing, roll coating or other known form of applying a coating to a support surface. Alternatively, the solidification process may be based on phase separation relying on induced thermodynamic demixing of a homogeneous polymer-solvent solution into a polymer-rich phase and a polymer-poor phase. This occurs usually by either exposure of the solution to another immiscible solvent or by cooling the solution below a binodal solubility curve. Thermal induced phase separation (TIPS) is one of the preferred scaffold manufacturing technique used.

Initially the surface polymer and block copolymer are mixed in a common solvent. As for the chemical nature of suitable common solvents, particular classes of various organic compounds have been found useful, including aliphatic and aromatic acids, aliphatic, aromatic and cyclic alcohols, aldehydes, primary and secondary amines, aromatic and ethoxylated amines, diamines, amides, esters and diesters, ethers, ketones and various hydrocarbons and heterocycles. Despite the diverse array of potentially suitable solvents, those skilled in the art will appreciate that the suitability of a particular solvent can be quite selective. Thus, for example, not all aromatic acids will be useful as a solvent for a given polymer and, further, not all solvents useful to dissolve a polymer such as polyethylene will necessarily be useful to dissolve a polymer such as polyvinylchloride.

As a convenient point of reference only, in the context of the present invention a person skilled in the art might consider a material(s) a "solvent" if at the required temperature it is capable of dissolving at least 0.5% (w/v) in total of the at least two immiscible polymers. Conversely, a material might be considered a "non-solvent" if at the required temperature it is not capable of dissolving at least 0.5% (w/v) in total of the at least two immiscible polymers. Preferably, the solvent will be capable of dissolving at least 1, more preferably at least 2, most preferably at least 5% (w/v) in total of the at least one surface polymer and at least one block copolymer.

In performing the method of the invention it may be desirable to include a non-solvent in the liquid composition to facilitate the formation of the phase separated composition. The addition of a non-solvent will generally cause an increase in the interaction parameter between the common solvent and the immiscible polymers and facilitate phase separation of the liquid composition. The non-solvent will generally be selected such that it is miscible with the at least one common solvent. It will be appreciated that as the proportion of non-solvent in the liquid composition is increased, the solubility of the at least one surface polymer and the at least one block copolymer in the liquid composition will correspondingly be decreased. It will also be appreciated that a material which functions as a solvent for one polymer may function as a non-solvent for another polymer, and vice versa. Thus, when a non-solvent is to be used in accordance with the method of the invention it can be selected using the general principles outlined above.

Examples of suitable common solvents, or non-solvents as the case may be, that may be used to prepare the porous polymer blend structures include, but are not limited to, dimethyl oxalate (DMO), ethylene carbonate (EC), N-methyl acetamide (NMA), dimethyl sulfoxide (DMSO), acetic acid (AA), 1,4-dioxane (DO), dimethyl carbonate (DMC), chloroform, dichloromethane (DCM), naphthalene, sulfalene, trimethylurea, ethylene glycol or other glycols and polyglycols, N-methyl pyrrolidone (NMP), ethylene carbonate, hexane, cyclohexane, trifluoroethanol (TFE), ethanol, acetic acid, and water, and combinations thereof.

Given the diverse array of polymers that may be used in accordance with the invention, it will be appreciated that it would be impractical to provide a comprehensive list of immiscible polymer combinations that may be used. Nevertheless, having regard to the general guidelines set forth above for determining whether a combination of polymers are immiscible, suitable polymers in general can be broadly classified as thermoplastic polymers. Suitable polymers can also exhibit a limited degree of cross-linking provided that they can still be dissolved in the common solvent.

Suitable polymers include, but are not limited to, low density polyethylene, high density polyethylene, polypropylene, polystyrene, polyacrylic acid and copolymers of polyacrylic acid and polystyrene, polyurethane, polyvinylchloride, polyvinylflouride, acrylonitrile-butadiene-styrene terpolymers, styrene-acrylonitrile copolymers, styrene butadiene copolymers, poly(4-methyl-pentene-1), polybutylene, polyvinylidene chloride, polyvinyl butyral, polyvinyl imidazole, chlorinated polyethylene, polyethylene oxide, ethylene-vinyl acetate copolymers, polyvinyl acetate, polyvinyl alcohol, polymethyl-methacrylate, polymethyl-acrylate, ethylene-acrylic acid copolymers, ethylene-acrylic acid metal salt copolymers, chlorosulphonate polyolefins, polyesters such as polyethylene teraphthalate and polybutylene teraphthalate, polyamides such as Nylon 6, Nylon 11, Nylon 13, Nylon 66, polycarbonates and polysulfones, and polyarylene and polyalkylene oxides; agrose, cellulose, gelatin, alginate, elastin, Chitosan, poly(lactide)s, poly(glycolide)s, poly(lactide-co-glycolide)s, poly(lactic acid)s, poly(glycolic acid)s, poly(lactic acid-co-glycolic acid)s, polycaprolactone, polycarbonates, polyesteramides, polyanhydrides, poly(amino acids), polyorthoesters, poly(hydroxyalkanoates), polyacetyls, polycyanoacrylates, polyetheresters, poly(esters), poly(dioxanone)s, poly(alkylene alkylate)s, copolymers of polyethylene glycol and polyorthoester, poly(hydroxy acids), poly(lactones), poly(amides), poly(ester-amides), poly(amino acids), poly(an hydrides), poly(ortho-esters), poly(carbonates), poly (phosphazines), poly(thioesters), polysaccharides and mixtures, blends and copolymers thereof.

The method of the invention is particularly suitable for making polymer structures or polymer coatings on a support surface, or substrate surface, that may be used as surface conditioners in culture ware, as bioreactor platforms, bioassay platforms, microbeads for cell culture or as 3-D scaffolds in tissue engineering applications. Polymers used in these applications will generally be biocompatible and are preferably biodegradable. In addition to acting as adhesive substrates for cells, such polymers should also promote cell growth and allow retention of differentiated cell function, possess physical characteristics allowing for large surface to volume ratios, have sound mechanical properties and have an ability to be formed into complex shapes, such as for bone or cartilage substitutes.

The polymer structure formed may be a film of surface polymer with functionalised islands or functional surface domains of polymer B block grouped on the surface of the surface polymer film. It has been observed that if the B and C blocks are the same hydrophobicity and both are hydrophilic then surfaces formed with these B blocks are able to absorb water molecules onto the surface of the surface polymer. This provides the opportunity for a hydratable gel like surface to be presented as a monolayer or gel layer for cell or molecule adhesion.

Mechanical rigidity is an important property of polymers used in tissue engineering applications. Relatively high rigidity is advantageous to enable the porous polymer structure to withstand the contractile forces exerted by cells growing within the structure. The resulting polymer structure should also be rigid, enough to maintain the desired shape under in vivo temperatures. Accordingly, the glass transition temperature(s) ($T_g$), as measured by Differential Scanning Calorimetry (DSC), of the polymer blend per se is preferably sufficiently high that the network of pores in the polymer structure does not collapse in vivo. A further parameter to consider when selecting a polymer for use in tissue engineering applications is the biodegradation kinetics of the polymer. In particular, it may be desirable that the biodegradation kinetics of the polymer match the healing rate associated with the specific in vivo application.

Examples of suitable surface polymers that may be homopolymers used to make polymer structures or coatings on support surfaces for use in tissue engineering applications include, but are not limited to, naturally derived polymers (eg collagen, chitin, hyaluronic acid, fibrin and alginates), and synthetic polymers (eg poly($\alpha$-hydroxyesters) such as PLGA, poly(anhydrides), poly(phosphazenes), polyorthoesters, polyurethanes and acrylate-based polymers).

Block copolymers which may be used with these surface polymers include the above listed polymers (ie those suitable as surface polymers) formed as a block copolymer with, for eg, polyethylene oxide (PEO), poly acrylic acid (PM), polyisoprene (PIP), poly tetra butyl acrylate (PTBA), Polyvinylpyrrolidone (P4VP), and Polymethylmethacrylate (PMMA).

Other polymers suitable for use in tissue engineering applications include the polycarbonates, polyimino-carbonates, polyarylates and polyurethanes.

An important criterion for producing the nanodomains in the surface of the surface polymer surface is the selection of an appropriate block copolymer for the given surface polymer. As mentioned above, the block copolymer has the general formulae A-B-C. According to the invention, A is a polymer of the same polymer type as the surface polymer or a polymer which is miscible or partially immiscible in the surface polymer; and B is a polymer having a higher level of immiscibility to polymer A.

All but very similar polymer materials display at least some degree of immiscibility with each other. Those skilled in the art will appreciate that two polymers will generally be considered "immiscible" if, upon being melt mixed, they do not form a homogeneous polymer mixture when molten or upon solidifying.

On this basis, the miscibility or immiscibility of a given pair of polymers may be determined using techniques well known in the art. For example, the two polymers may be melt mixed and the presence or absence of phase separated domains in the blend determined using microscopy techniques such as scanning or transmission electron microscopy (SEM or TEM, respectively). The glass transition temperature(s) (Tg) of a blend of two polymers can also be measured by Differential Scanning Calorimetry (DSC) and used as a guide to determine whether the polymers are immiscible. In this case, if the polymer blend is found to have two Tgs, then the polymers are likely to be immiscible. On the other hand, if only one Tg for the polymer blend is observed, then the polymers are likely to be miscible.

It may of course be possible to force two polymers that are otherwise immiscible to become miscible by subjecting them to high temperature and pressure. However, while being forced to be miscible under these extreme conditions, such a polymer blend will typically phase separate upon being allowed to cool naturally to room temperature.

Examples of specific combinations comprising at least one block copolymer combined with at least one surface polymer therefore include, but are not limited to, those based on polystyrene/poly(acrylic acid) (PS/PAA) block copolymers combined with polystyrene surface polymers, polystyrene/poly (ethylene oxide) (PS/PEO) block copolymers combined with polystyrene surface polymer, poly(lactic-co-glycolic acid)/ poly-l-lysine (PLGA/PLL) block copolymer combined with PLGA surface polymer, polystyrene/polyisoprene (PS/PIP) block copolymer combined with PS surface polymer, polystyrene/polymethyl methacrylate (PS/PMMA) block copolymer combined with PS surface polymer, and polystyrene/ polymethyl methacrylate (PS/PMMA) block copolymer combined with poly (ethylene oxide) (PEO) surface polymer.

The liquid composition used in accordance with the invention will generally be prepared by heating the at least one surface polymer and at least one block copolymer and the at least one common solvent with mixing to a temperature required to dissolve a sufficient amount of the polymers in the solvent. Preferably, substantially all of the polymers used will be dissolved in the solvent. In some circumstances, it may be desirable to dissolve each of the polymers separately into a portion of the common solvent and then mix the dissolved polymers to settle to form the liquid composition. More preferably the liquid composition is formed and held at a temperature above the binodal temperature of the at least two immiscible polymers. It is also preferred that the surface polymer and block copolymer are dissolved in the at least one common solvent to form a homogenous liquid.

To prepare a polymer structure having a plurality of surface domains in accordance with a preferred form of the present invention the liquid composition forms a phase separated composition. Scaffold manufacturing or micro-bead preparation techniques based on phase separation rely on induced thermodynamic demixing of a homogeneous polymer-solvent solution into a polymer-rich phase and a polymer-poor phase, usually by either exposure of the solution to another immiscible solvent or by cooling the solution below a binodal solubility curve. Thermal induced phase separation (TIPS), which as stated previously, will be the predominant manufacturing technique used for scaffolds and microbeads. The technique uses the thermal energy as a latent solvent to induce phase separation.

The polymer solution is quenched below the freezing point of the solvent and subsequently freeze-dried to produce porous structures or coated on an appropriate substrate. One of the significant advantages of this technique over other scaffold manufacturing techniques is that various structures can be easily obtained by adjusting various thermodynamic and kinetic parameters. According to Flory, in three-component systems composed of a polymer, solvent and non-solvent, two types of phase separation phenomena can be distinguished. One type is polymer-poor liquid vs polymer-rich liquid phase separation and the other type is liquid vs polymer phase separation. According to the second law of thermodynamics, liquid-liquid phase separation occurs in an attempt to lower the overall Gibbs free energy. This separation usually happens if the solvent is a relatively poor for the chosen polymer. Also, in liquid-liquid separation, there is a possibility of equilibrium between the liquid phase and polymer phase when the temperature is lowered. Solid-liquid phase separation usually takes place in a good solvent-polymer system.

The criteria for miscibility in any two component polymer-diluent system can be expressed in terms of the Gibbs free energy of mixing, $\Delta G_{mix}$ and its second derivative with respect to polymer volume fraction, $\phi_2$, at fixed temperature, T and pressure, P, $$\Delta G_{mix} < 0, \tag{1}$$

$$(\delta^2 \Delta G_{mix} / \delta \phi_2^2)_{T,P} > 0, \tag{2}$$

where $\Delta G_{mix} = \Delta H_{mix} - T\Delta S_{mix}$, with $\Delta H_{mix}$ and $\Delta S_{mix}$ representing the enthalpy and entropy of mixing, respectively

[Lloyd D. R., et al, J. Membrane Sci 1991; 64(1-2):1-11]. If either criterion is not met, the solution may separate into two phases in equilibrium.

Figure 9:
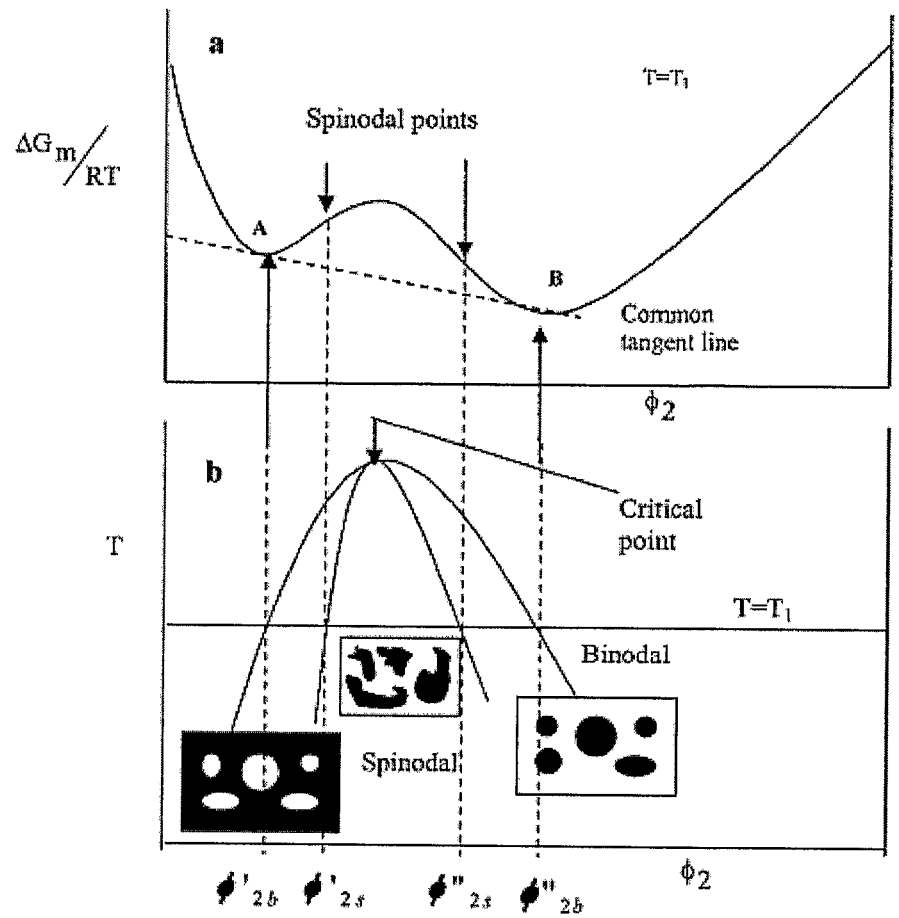
FIG. 9 illustrates the correlation between Gibbs free energy of a liquid composition with its binodal and spinodal curves of a phase diagram.

In the case of a partially miscible system, a homogeneous one-phase solution is formed only under certain conditions of composition and temperature. If a common tangent line is drawn on the $\Delta G_{mix}/RT$ versus $\phi_2$ plot, as shown in FIG. 9, the co-tangential points are called binodal points ($\phi'_{2b}$ and $\phi''_{2b}$). At the binodal points at $T=T_1$, equations (3) and (4) must be satisfied.

$$\left[\frac{\partial(\Delta G'/RT)}{\partial \phi_2}\right]_{\phi_2=\phi'_{2b}} = \left[\frac{\partial(\Delta G'/RT)}{\partial \phi_2}\right]_{\phi_2=\phi'_{2b}} \quad (3)$$

$$(\Delta G'_m/RT)' - \left[\frac{\partial(\Delta G'_m/RT)}{\partial \phi_2}\right]_{\phi_2=\phi'_{2b}} \phi'_{2b} = \quad (4)$$

$$(\Delta G'_m/RT)'' - \left[\frac{\partial(\Delta G'/RT)}{\partial \phi_2}\right]_{\phi_2=\phi'_{2b}} \phi''_{2b}$$

Figure 8:
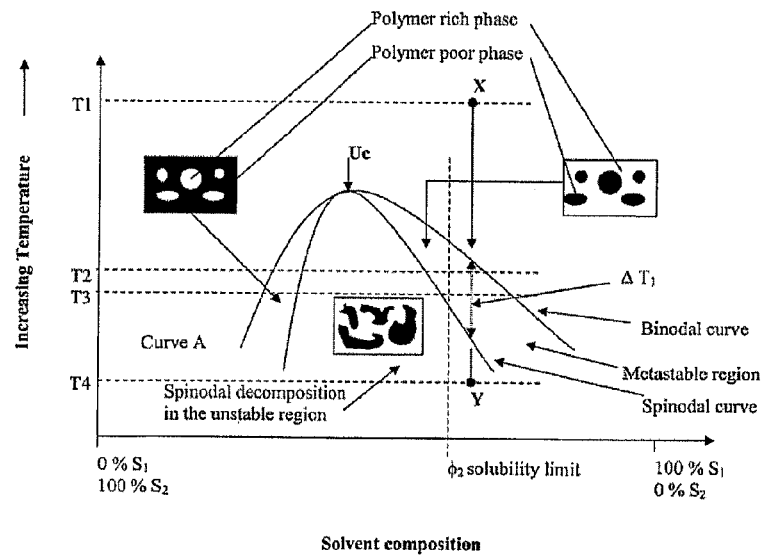
FIG. 8 depicts a typical polymer solution phase diagram for a polymer-solvent/non-solvent system at a nominal polymer concentration.

The locus of the binodal points at various temperatures makes a binodal curve. As shown in FIG. 8, at the spinodal points ($\phi'_{2s}$ and $\phi''_{2s}$) equation (5) is satisfied at a certain temperature ($T=T_1$):

$$(\delta^2 \Delta G_{mix}/\delta \phi_2^2)_{T,P}=0, \quad (5)$$

The spinodal points at various temperatures make a locus called a spinodal curve (FIG. 9). Below the spinodal curve, the system is unstable and spinodal decomposition occurs. Spinodal decomposition is a kinetic process of generating within an unstable mother phase a spontaneous and continuous growth of another phase. The growth originates from small amplitude composition fluctuations which statistically promote continuous and rapid growth of the sinusoidal composition modulation with a certain maximum wavelength (Olabisi O. Polymer-polymer miscibility, New York: Academic Press, 1979). The decomposed system is characterized at some point by a high level of phase interconnectivity in both the minor and major phases—a structure which could possess unusual mechanical and permeability characteristics.

The rate at which the temperature of the liquid composition is reduced is believed to be an important parameter for causing the polymers to phase separate into a common polymer rich phase and a common polymer poor phase. In particular, it is believed that the rate of cooling should be sufficient to promote spinodal decomposition of at least a proportion of the liquid composition.

As will be discussed in more detail below, provided that at least some spinodal decomposition of the liquid composition occurs (to thereby cause phase separation of the polymers into a common polymer rich phase), a proportion of the liquid composition may also undergo binodal decomposition.

Binodal decomposition of the liquid composition is generally less preferred as this typically results in the sequential phase separation of each of the polymers into different polymer rich and polymer poor phases, which results in the formation of a phase separated polymer blend lacking interconnectivity of pores. Accordingly, the temperature of the liquid composition is reduced such that preferably at least 50% by volume, more preferably at least 65% by volume, most preferably at least 85% by volume undergoes spinodal decomposition.

In addition to reducing the temperature of the liquid composition to promote phase separation, a non-solvent may be introduced into the liquid composition to facilitate phase separation. Given that it will be necessary to ultimately remove most if not all solvent/non-solvent from the phase separated composition, the introduction of a non-solvent is less preferred.

Thermally induced phase separation (TIPS) is a known technique for producing porous polymers through the phase separation of liquid compositions. This technique may be conveniently applied in performing the method of the invention. TIPS is generally conducted by first dissolving a polymer in a solvent or solvent/non-solvent mixture and then lowering the temperature of the solution to induce liquid-liquid or solid-liquid phase separation. The phase separation results in polymer-rich and polymer-poor phases being formed within the solution. After solidifying one or both of the polymer-rich or polymer-poor phases, the polymer-poor phase is removed leaving a highly porous polymer structure.

Performing the invention using TIPS has a number of advantages over other techniques that may be used to promote phase separation of the liquid composition. TIPS is relatively simple to apply and can be performed at relatively low cost. The technique enables the morphology of the resulting surface on the polymer structure to be tailored through variation of processing parameters such as polymer concentration, solvent/non-solvent type, solvent/non-solvent ratios and thermal quenching strategies such as quenching temperature and quenching rate. In conducting TIPS, cooling parameters for the polymer solution play an important role in determining the morphology of the resultant surface on the polymer structure. During cooling of a polymer solution, solid-liquid phase separation can occur as a result of solvent freezing or polymer precipitation. A non-solvent may be included in the polymer solution to promote liquid-liquid phase separation. FIG. 8 represents a typical polymer solution phase diagram for a polymer-solvent/non-solvent system at a nominal polymer concentration. The Y-axis defines temperature, with T2 representing the glass transition temperature (Tg) of the polymer and T3 the solidification temperature of the solvent. These temperatures correspond to solid-liquid phase separation. The X-axis defines the solvent/non-solvent composition, with $S_1$ representing the solvent and $S_2$ representing the non-solvent $\phi_2$ defines the solubility limit of a polymer at a specific solvent composition, whereby the polymer is substantially insoluble in solvent compositions to the left of the limit, but soluble enough to form a solution in solvent compositions to the right of the limit.

The upper and lower parabolic-like curves in FIGS. 8 and 9 are known as the binodal and spinodal curves, respectively. In regions defined above the binodal curve, the polymer solution exists as a stable single-phase system, whereas in regions below the binodal curve the polymer solution exists as a metastable or unstable two-phase system. In particular, the spinodal curve demarcates the two-phase region into metastable and unstable regions, with the metastable region being defined between the binodal and spinodal curves, and the unstable region being defined below the spinodal curve. The point Uc on the curves represents the maximum temperature at which spinodal decomposition may occur.

When the temperature of a polymer solution is reduced such that it passes from the single-phase region into the two-phase region, the solution may undergo phase separation by a nucleation and growth mechanism in the metastable region (binodal decomposition), or a spinodal decomposition mechanism in the unstable region. FIG. 8 illustrates the morphology of the two-phase separated systems that form through each phase separation mechanism. The nucleation and growth mechanism, which occurs in the metastable region, provides for isolated spheroidal domains within a continuous phase domain, whereas the spinodal decomposition mechanism, which occurs in the unstable region, provides for bi-continuous phase domains that give rise to interconnected pores.

The final morphology of a polymer structure formed by TIPS can be "fixed" by quenching the two-phase structure-formed composition to a temperature at or below the glass transition temperature of the polymer (T2 in FIG. 8) and/or at or below the freezing temperature of the solvent (T3 in FIG. 8) (herein after referred to as the "solidification temperatures"). Solvent/non-solvent can then subsequently be removed from the "fixed" porous polymer structure by sublimation, evaporation, or solvent extraction under appropriate conditions.

FIG. 8 also depicts a typical quenching regime which involves quenching the composition of the polymer solution defined at point X to point Y. Such a quenching regime will afford a polymer structure having a morphology which is at least in part derived through a spinodal decomposition mechanism. By this route, the polymer solution will generally first be heated to temperature T1 to provide for a single-phase polymer solution. The solution is then cooled to temperature T4, and in doing so passes through the metastable region (defined between the binodal and spinodal curves) and into the unstable region (defined below the spinodal curve). Under this regime, the cooling rate will be the dominant factor in determining the operative phase separation mechanism, and hence also the resulting pore morphology of the porous polymer structure. If the cooling rate is sufficiently fast, the polymer solution can quickly pass through the metastable region and into the unstable region, where phase separation will be dominated by a spinodal decomposition mechanism. In contrast, if the cooling rate is relatively slow, the solution may have enough time to form nuclei in the metastable region and phase separation may be dominated by a nucleation and growth mechanism. Accordingly, the temperature range defined by $\Delta T_1$ can also influence the operative phase separation mechanism. That is, where $\Delta T_1$ is large in passing from point X to point Y, the likelihood of at least some phase separation occurring by a nucleation and growth mechanism increases.

The practical operating window for performing the method of the invention using TIPS can vary as a function of temperature, polymer concentration, and/or solvent or solvent/non-solvent composition for a specific liquid composition. Phase diagrams can provide considerable detail on the relationship between temperature, polymer concentration, and solvent/non-solvent compositions for a given liquid composition. Such diagrams can therefore be used to assist in the preparation of an appropriate liquid composition for a given polymer/solvent or polymer/solvent/non-solvent system when performing the method of the invention. Phase diagrams for a number of polymer/solvent or polymer/solvent/non-solvent systems are generally known to those skilled in the art. However, where a specific phase diagram is not available, the curves can be determined by known techniques. For example, a suitable technique is described in Flory P. J. Principles of polymer chemistry, Ithaca:Cornell University Press, 1953; Olabisi O. Polymer-polymer miscibility, New York: Academic Press, 1979.; Lloyd D. R., Kim S. S. and Kinzer K. E. Journal of Membrane Science 1991; 64(1-2):1-11; Kim S. S. and Lloyd D. R. Polymer 1992; 33(5):1047-57; and Flory P. J. Discussions of the Faraday Society 1970; No. 49(7-29.

To form the polymer structure in accordance with a preferred form of the invention, it will be necessary to solidify the polymers in the common polymer rich phase onto the surface of a substrate. Where the phase separated liquid composition is at a temperature above the "solidification temperatures", solidification of the polymers may be initiated by reducing the temperature of the liquid composition to below the glass transition temperature of the polymers and/or below the freezing temperature of the at least one common solvent.

Where the phase separated composition is at a temperature equal to or below the "solidification temperatures", the liquid composition will be in a supercooled state and therefore will not generally require further impetus to cause the polymers to solidify. In other words, the polymers in the common polymer rich phase will generally automatically solidify. It will be appreciated that the rate of such solidification will generally be greater as the temperature differential between the supercooled liquid composition and the "solidification temperatures" increases.

Typically, the rate at which the polymers in the common polymer rich phase solidify will determine the degree of phase separation that occurs between these polymers. Through manipulation of the solidification rate (i.e. ageing time), the physical composition of the struts that make up the polymer structure can advantageously be tailored. Thus, a rapid rate of solidification that essentially provides little or no ageing of the common polymer rich phase can result in the substantially all of the polymers being fixed into a molecularly mixed state. If the solidification rate is reduced to enable the common polymer rich phase to age, a degree of phase separation of the polymers can occur. By rapid solidification of the polymer rich phase, it may be possible that a solid can be produced where the non-surface polymer domain of the block copolymer (ie B block) has not been able to fully separate into surface domains and is mixed throughout the surface polymer. In cases where this is possible it provides the opportunity to age the polymer by the application of localised heat to the surface of the formed polymer structure encouraging migration of the block copolymer to a thermodynamically lower state at the surface, thus forming non-surface polymer domains (ie B block) in proximity to the heat source. Thus, provided the surface polymer is melt processable at the temperature of the applied localised heat source, then the position of the non-surface polymer domains (ie B block) can be controlled. This is more applicable to a surface coating application than a scaffold. It is believed that a PS/PMMA block copolymer in a PS surface polymer provides such a thermally stable system.

In a preferred embodiment of the present invention the liquid composition comprising the polymers dissolved in the common solvent is maintained at a temperature above the binodal temperature for the at least two immiscible polymers to form a homogenous solution. The temperature of this homogenous solution is then reduced to a temperature below the spinodal temperature of the polymers at a rate that substantially avoids the formation and maturation of a binodal composition. Having "fixed" the phase separated morphology of the polymer blend, it will be necessary to remove the common polymer poor phase from the composition to form the surface of the structure. For example, the common polymer poor phase (which will typically comprise predominantly solvent or solvent/non-solvent) may be removed by extracting it with a further suitable solvent that is a non-solvent for the polymer structure. The relative miscibility or solubility of the common polymer poor phase in such a further solvent will, in part, determine its effectiveness in terms of the time required for extraction. The extracting or leaching process can be carried out at an elevated temperature below the softening point of the polymer blend to reduce the extraction time.

Removal of the common polymer poor phase may also be achieved by other known techniques. Illustrative examples of such techniques include, but are not limited to, evaporation and sublimation.

The time required to effect removal of the common polymer poor phase will vary depending upon the technique employed, the type of extracting solvent or non-solvent used, the temperature used and the degree of extraction required. In some instances, it may be unnecessary to extract all of the common polymer poor phase from the polymer structure. The amount of residual polymer, common solvent or common solvent/non-solvent from the common polymer poor phase that can be tolerated will primarily depend upon the requirements of the intended end use application of the polymer.

C may be a chemical groups/moieties selected from the group including (male)imides, —COOH, —SH, —$SO_4^{2-}$, $PO_4^{3-}$, —$NH_3$, -vinyl sulphone, -epoxy, -alkyne, -hydrazide, -aldehyde (these last 4 moieties allow 'click' chemistry to be utilised), as well as hydrophobic (lipid-like) groups such as —$C(CH_3)_3$, —$C_6F_5$, known cell binding domains from extracellular matrix molecules (ligands), for example laminin, fibronectin, vitronectin and collagen (e.g. YIGSR, PDSGR, IKVAV, RGDN), and others as would be known to those skilled in the art.

Examples of biologically active compounds that may be attached to the surface of polymer structures or polymer coating surfaces include, but are not limited to, cell attachment mediators, such as the peptide containing variations of the "RGD" integrin binding sequence known to affect cellular attachment, biologically active ligands, and substances that enhance or exclude particular varieties of cellular or tissue ingrowth. Such substances include, for example, osteoinductive substances, such as bone morphogenic proteins (BMP), epidermal growth factor (EGF), fibroblast growth factor (FGF), platelet-derived growth factor (PDGF), insulin-like growth factor (IGF-I and II), TGF-β, trypsin, anti-fouling enzymes and the like.

Examples of pharmaceutically active compounds that may be attached to the surface of polymer structures or polymer coating surfaces include, but are not limited to, acyclovir, cephradine, malfalen, procaine, ephedrine, adriomycin, daunomycin, plumbagin, atropine, guanine, digoxin, quinidine, biologically active peptides, chlorin $e_6$, cephalothin, proline and proline analogues such as cis-hydroxy-L-proline, penicillin V, aspirin, ibuprofen, steroids, nicotinic acid, chemodeoxycholic acid, chlorambucil, and the like. Therapeutically effective dosages may be determined by either in vitro or in vivo methods. For each particular additive, individual determinations may be made to determine the optimal dosage required. The determination of effective dosage levels, that is, the dosage levels necessary to achieve the desired result, will be within the ambit of one skilled in the art. The release rate of the additives may also be varied within the routine skill in the art to determine an advantageous profile, depending on the therapeutic conditions to be treated.

Example 1

A-B-C Block Copolymer System of PS-PEO-Carboxylic Acid

This example demonstrates the production of an A-B-C block copolymer system where the addition of a terminal C group, carboxylic acid, to an A-B diblock copolymer of PS-PEO, which does not affect the phase behaviour of A-B diblock copolymer system but allows for the attachment of another molecule to the C group (ie, in this example an amine containing fluorescent dye was conjugated to C terminal groups on the generated surface). The use of an amine containing fluorescent dye allows for a simple determination of the effectiveness of the conjugation via fluorescence microscopy and since most biologically relevant molecules contain an amine group binding this example is representative of the final application of this method.

Polymer Properties

| Polymer | Mn (kDa) | | | Polydispersity Index |
| --- | --- | --- | --- | --- |
| | A | B | Total | |
| PS | — | — | 202 | 1.05 |
| PS-PEO | 51 | 11.5 | 62.5 | 1.05 |

Addition of Terminal Carboxylic Acid Group to PEO

A solution of 40 mg/mL of PS-PEO and 2 mg/mL of succinic anhydride was stirred for 4 hours at 60° C. The addition of a carboxylic acid occurs via the reaction of succinic anhydride with the terminal hydroxyl group of the PEO (Scheme 1). The reaction products were then recovered by removal of the solvent in vacuo, re-dissolved in chloroform and precipitated drop-wise into methanol. The precipitate was vacuum filtered and washed extensively with methanol and water to remove any unreacted succinic anhydride. The remaining white powder was then dried overnight in a vacuum oven at 40° C. $^1$H NMR was used to confirm the addition of a carboxylic acid to the terminal hydroxyl group.

Scheme 1. Reaction of polystyrene-b-polyethylene oxide with succinic anhydride to yield carboxylic acid functionalized polymer (A-B-C).

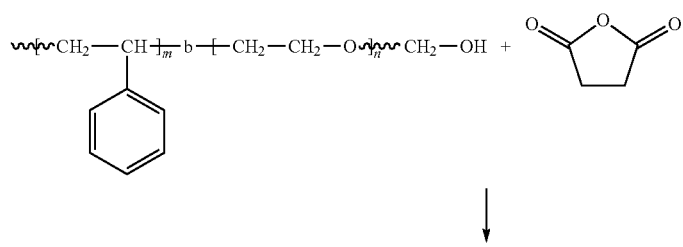

-continued

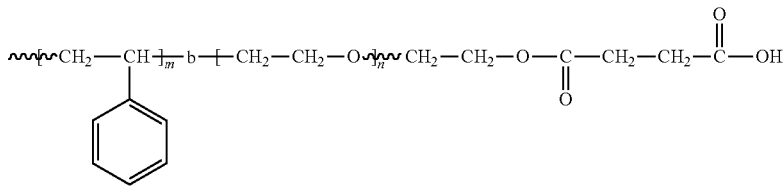

Substrate Preparation and Spin Casting

Silicon wafers were cut into 2 cm squares before being rinsed thoroughly in acetone, followed by isopropanol and dried under a stream of nitrogen. The wafers were then exposed to UV/ozone for 10 minutes to remove any remaining organics and to generate a uniform silicon oxide ($SiO_2$) surface layer. Thin films were generated by spin casting at 2000 rpm from polymer solutions containing 1 wt % total polymer concentration in toluene. These films, or surfaces, are also referred to herein as A-B-C surfaces, block copolymer (BCP), and/or block copolymer nano-pattern (BCN).

Conjugation of Amine Containing Fluorescent Dye to Surface

A solution of 2 mg/mL of Alexa fluor 488 cadaverine salt with 50 µg/ml N-hydroxysuccinimide (NHS) and 50 µg/ml 1-ethyl-3-(3-dimethylaminopropyl)carbodiimide (EDAC) in water was incubated on the surface of the spin cast films overnight at 4° C. The conjugation of the dye occurs via the reaction of NHS to carboxylic acid on the PEO and then the further reaction with the amine group on the dye. The films were then thoroughly rinsed with water to remove any unbound dye. The binding of the dye was assessed using fluorescence microscopy.

Figure 2:
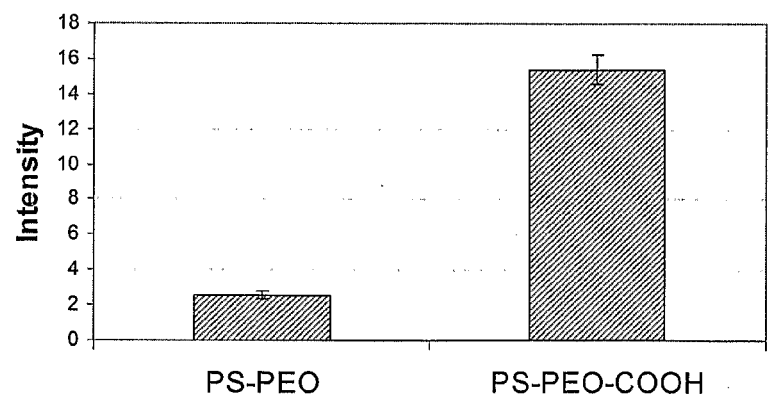
FIG. 2 Image analysis results for films of PS-PEO and PS-PEO-COOH.
Figure 3:
FIG. 3 Fluorescence image of a PS-PEO-COOH film that has had fluorescent dye conjugated to it and has been scratched in order to demonstrate the fluorescence.

The addition of a terminal C group, in this instance a carboxylic acid, has not affected the micro-phase separation behaviour of the PS-PEO copolymer (FIG. 1). However, the addition of a terminal acid group has facilitated the conjugation of an amine containing dye, as evidenced by the ~7× increase in fluorescence intensity compared to the non-functionalised PS-PEO film (FIG. 2 and FIG. 3).

Example 2

A-B-C Block Copolymer System of PS-PEO-Maleimide Group

This example demonstrates the production of an A-B-C block copolymer system where the addition of a terminal C group, maleimide group, to an A-B diblock copolymer of PS-PEO, which does not affect the phase behaviour of A-B diblock copolymer system but allows for the attachment of another molecule. Maleimide groups react specifically with thiol groups forming a stable carbamate bond. Thiol groups are present as side chains on the amino acid cysteine, this maleimide terminal group therefore allows for specific conjugation of biologically relevant molecules.

Polymer Properties

| Polymer | Mn (kDa) | | | Polydispersity Index |
| | A | B | Total | |
|---|---|---|---|---|
| PS | — | — | 202 | 1.05 |
| PS-PEO | 51 | 11.5 | 62.5 | 1.05 |

Addition of Terminal Maleimide Group to PEO

A solution of 50 mg/ml of PS-PEO and 8 mg/ml of N-(p-Maleimidophenyl)isocyanate (PMPI) (Pierce, Rockford, Ill.) in dimethyl formamide (DMF) was stirred for 4 hours at room temperature. The addition of a maleimide group occurs via the reaction of isocyanate with the terminal hydroxyl group of the PEO (Scheme 2). The reaction products were then recovered by removal of the solvent in vacuo, re-dissolved in chloroform and precipitated drop-wise into methanol. The precipitate was vacuum filtered and washed extensively with methanol and water to remove any unreacted PMPI. The remaining yellowish powder was then dried overnight in a vacuum oven at 40° C. $^1$H NMR was used to confirm the addition of a maleimide to the terminal hydroxyl group.

Scheme 2. Reaction of polystyrene-b-polyethylene oxide with PMPI to yield maleimide functionalized polymer (A-B-C).

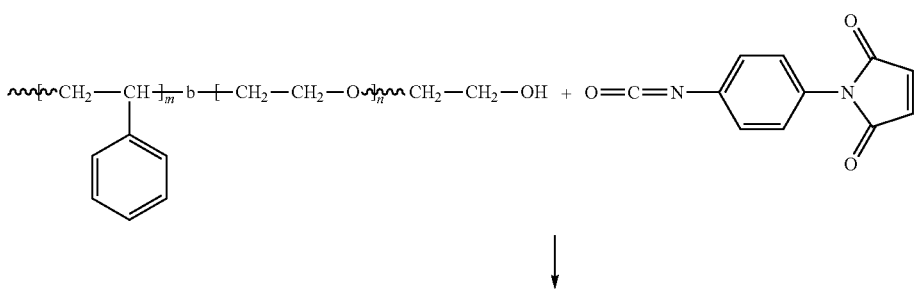

-continued

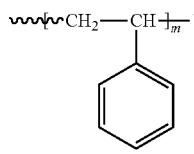 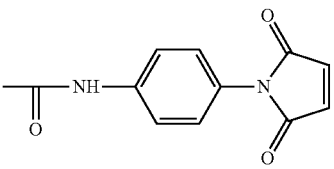

Substrate Preparation and Spin Casting

Silicon wafers were cut into 2 cm squares before being rinsed thoroughly in acetone, followed by isopropanol and dried under a stream of nitrogen. The wafers were then exposed to UV/ozone for 10 minutes to remove any remaining organics and to generate a uniform silicon oxide ($SiO_2$) surface layer. Thin films were generated by spin casting at 2000 rpm from polymer solutions containing 1 wt % total polymer concentration in toluene.

Figure 4:
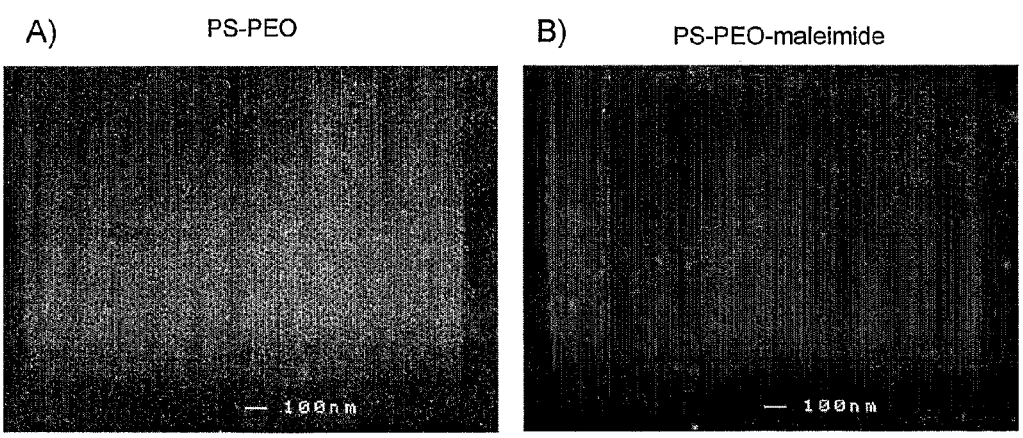
FIG. 4 Scanning electron micrograph of spin cast block copolymer films of a) PS-PEO and b) PS-PEO modified to have a terminal carboxylic acid group.

The addition of a terminal C group, in this instance a maleimide, has not affected the micro-phase separation behaviour of the PS-PEO copolymer (FIG. 4).

Example 3

Phase Behaviour of Polymer of Example 2

In this example we describe the microphase separation of the PS-PEO A-B diblock copolymer and terminally derivatized A-B-C block copolymer system during the 3-dimensional scaffold manufacture process. Microphase separation is shown to occur on scaffolds fabricated via TIPS for both liquid-liquid phase separating systems and solid-liquid phase separating systems.

Polymer Properties

| Polymer | Mn (kDa) | | | Polydispersity Index |
| --- | --- | --- | --- | --- |
| | A | B | Total | |
| PS | — | — | 202 | 1.05 |
| PS-PEO | 51 | 11.5 | 62.5 | 1.05 |

Addition of Terminal Maleimide Group to PEO

A solution of 50 mg/ml of PS-PEO and 8 mg/ml of N-(p-Maleimidophenyl)isocyanate (PMPI) (Pierce, Rockford, Ill.) in dimethyl formamide (DMF) was stirred for 4 hours at room temperature. The addition of a maleimide group occurs via the reaction of isocyanate with the terminal hydroxyl group of the PEO (Scheme 2 above). The reaction products were then recovered by removal of the solvent in vacuo, re-dissolved in chloroform and precipitated drop-wise into methanol. The precipitate was vacuum filtered and washed extensively with methanol and water to remove any unreacted PMPI. The remaining yellowish powder was then dried overnight in a vacuum oven at 40° C. $^1$H NMR was used to confirm the addition of a maleimide to the terminal hydroxyl group.

Scaffold Fabrication

Scaffolds were fabricated by TIPS. Dioxane solutions, which do not liquid-liquid demix, were quenched by solid-liquid phase separation. Cyclohexane and dimethyl carbonate (DMC) solutions were fabricated by liquid-liquid phase separation.

a. Solutions containing 7.5% (w/vol) of polystyrene, polystyrene-b-poly (ethylene oxide) block copolymer or polystyrene-b-poly (ethylene oxide) block copolymer with maleimide end group were heated to approximately 50° C. (or higher if necessary) on a hot plate for approximately 5 minutes, in order to completely homogenise the solutions.

b. Solid-liquid phase separated scaffolds were quenched in a temperature controlled bath at approximately −3° C. These crystallised after 5-20 minutes.

c. Liquid-liquid phase separated scaffolds were held in the bath at 15° C. for 15 minutes then immersed in liquid nitrogen for 1-2 minutes.

d. Solvent was removed from the scaffolds via vacuum drying at approximately $10^{-3}$ mbar for approximately 6 hours.

Figure 5:
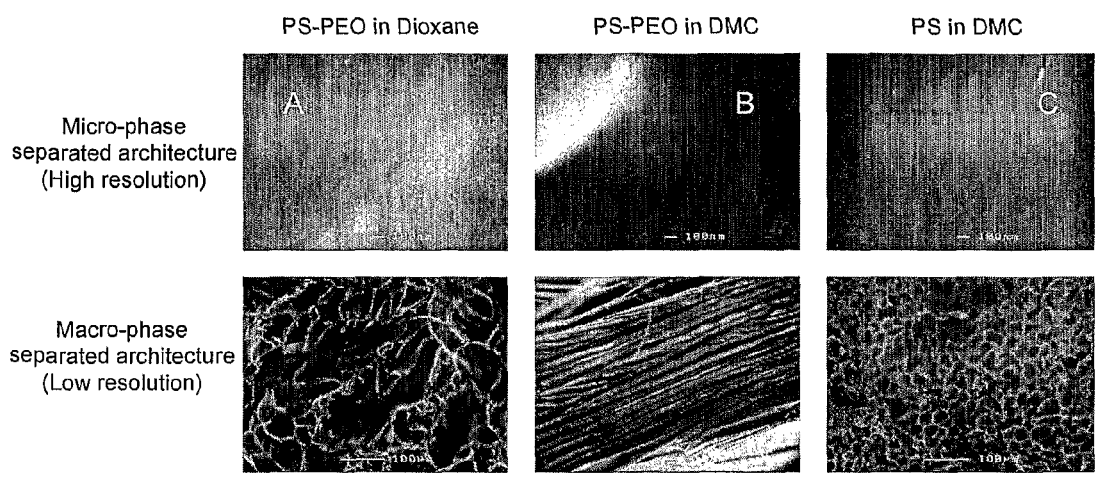
FIG. 5 SEM micrographs of PS-PEO and PS scaffolds manufactured from different solvents.
Figure 6:
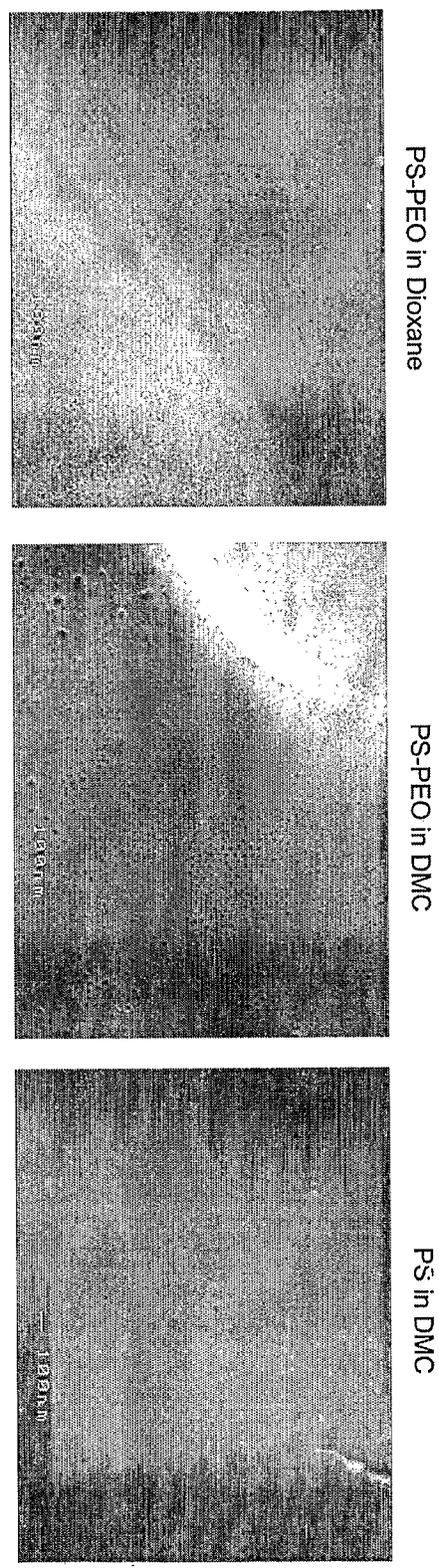
FIG. 6 Magnified version of the SEM micrographs labelled A, B and C in FIG. 5.

The resulting highly porous polymer scaffolds with surface functionality were imaged by SEM. From the micrographs in FIG. 5 and FIG. 6 it is evident that microphase separation has occurred in both the solid-liquid and liquid-liquid TIPS processes that contained PS-PEO block copolymer. However in the pure PS system there is no evidence of surface patterning. Furthermore a number of different macro-architectures are possible due to the different solvents and the use of the TIPS process.

Figure 7:
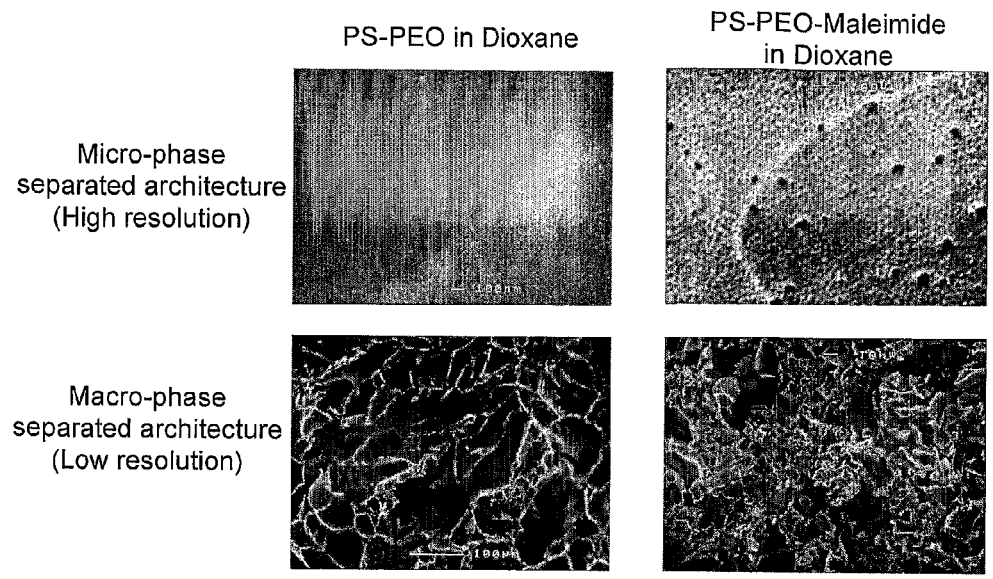
FIG. 7 Scanning electron micrograph of PS-PEO scaffolds manufactured by solid-liquid phase separation from dioxane. The micro-phase separation is not affected by the addition of the maleimide end group.

The addition of a terminal C group, maleimide group, to the A-B diblock copolymer of PS-PEO, does not affect the phase behaviour of the system (FIG. 7), but introduces a group that will allow for the attachment of another molecule.

Example 4

Fibroblast Behaviour, and Effect of Inter-Domain Spacing Thereon, for the Polymer of Example 2 Functionalised with RGD In this example we assess the behaviour of fibroblasts seeded onto a surface functionalised with the block copolymer of the invention.

Materials: Polystyrene-block-polyethylene oxide) (PS-PEO) and polystyrene (PS) were purchased from Polymer Source Pty. Ltd. (Montreal, PQ, Canada). HPLC grade toluene was purchased from Aldrich and used as supplied. Silicon wafers (100 orientation, Boron doped) were purchased from Micro Materials and Research Consumables Pty. Ltd.

Methods: PS-PEO block copolymer functionalised with maleimide terminal group as described previously (examples 2 and 3) was blended with polystyrene (from 100% block copolymer to 0% block copolymer) and spin cast from 1% toluene solution onto silicon wafers. Surfaces were then functionalised with a Cysteine containing CGRGDS moiety by immersion in a 100 ug/ml solution of the peptide in coupling buffer for 2 hours, before being rinsed thoroughly in PBS. 3T3-NIH Fibroblast cells were then seeded onto the surfaces at a density of 10000 cells/cm$^2$ in serum free conditions, cultured for 4 hours, and fixed and stained for nuclei and F-actin.

Figure 10:
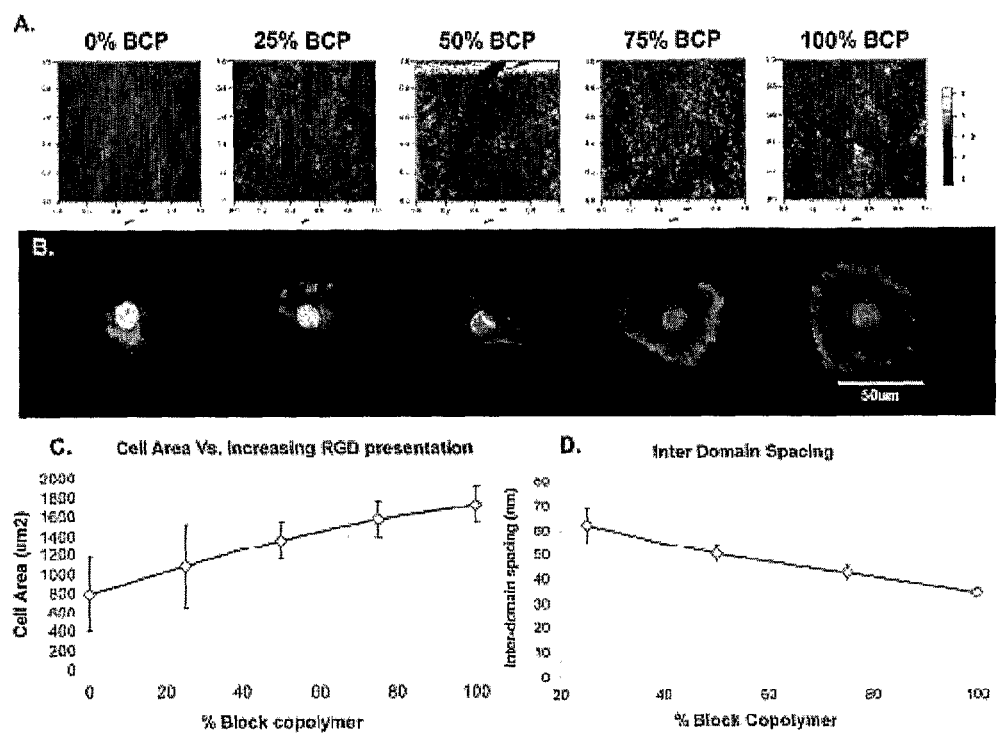
FIG. 10 illustrates the cellular response to different density of RGD (effected by introduction of different amounts of block copolymer).

Results: The spacing of RGD peptides can be controlled on the nanometer length scale by exploiting the self-assembly of functionalised PS-PEO block copolymers. FIG. 10 indicates that the density of PEO domains can be controlled by blending with polystyrene as previously described (George P, Cooper-White J. Kinetically constrained block copolymer self-assembly—a simple method to control domain size. European Polymer Journal 2009).

FIG. 10A are atomic force microscopy images of spin cast films indicating change in density of nano-domains with block copolymer concentration. In FIG. 10B, fluorescence image (actin shows as green (outer region), nuclei shows as blue (circular inner region))—cells spread more on surfaces presenting a higher density of RGD nano-domains. In FIG. 10C, cell area shows an increasing trend with increasing content of functionalised block copolymer and therefore RGD. In FIG. 10D, the inter-domain spacing of islands on the block copolymer film decreases with increasing block copolymer content.

The spreading of fibroblast cells is shown to increase on films presenting higher densities of RGD consistent with previous publications (Cavalcanti-Adam E A, Micoulet A, Blummel J, Auernheimer J, Kessler H, Spatz J P. Lateral spacing of integrin ligands influences cell spreading and focal adhesion assembly. European Journal of Cell Biology 2006; 85(3-4):219-224, Hirschfeld-Warneken V C, Arnold M, Cavalcanti-Adam A, Lopez-Garcia M, Kessler H, Spatz J P. Cell adhesion and polarisation on molecularly defined spacing gradient surfaces of cyclic RGDfK peptide patches. European Journal of Cell Biology 2008; 87(8-9):743-750). This result indicates the utility of self-assembly in generating bio-interactive materials which allow precise control over the surface presentation of ligands and bio-molecules.

Example 5

Figure 11:
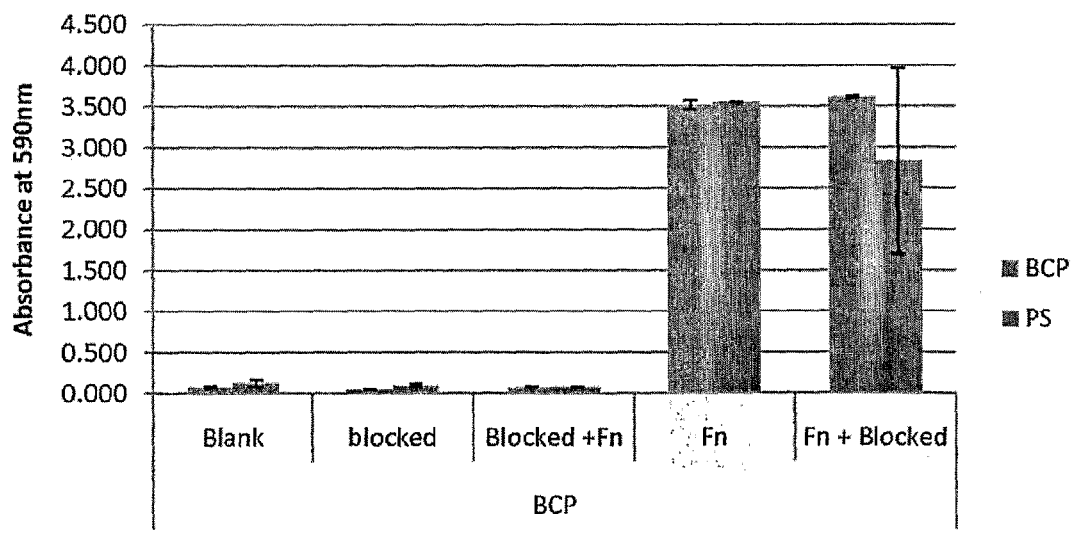
FIG. 11: The success of Synperonic F108 as a blocking agent for the A-B-C surface. The surfaces were prepared without any chemical modification, removing any specific binding of the protein. All protein adsorbed to the surface is via non-specific interactions. These interactions have been completely avoided by the blocking the A-B-C surface with Synperonic F108.

Fouling Characteristics of Surface of Polymer of Example 2 Functionalised with a Blocking Agent The A-B-C block copolymer system was prepared as in Example 2. Surfaces were then functionalised with polymeric blocking agent (Synperonic F108). This prevented non-specific protein adsorption to the surface (FIG. 11).

Example 6

Binding Mixed Protein Solutions to the Surface of Polymer of Example 2

Figure 12:
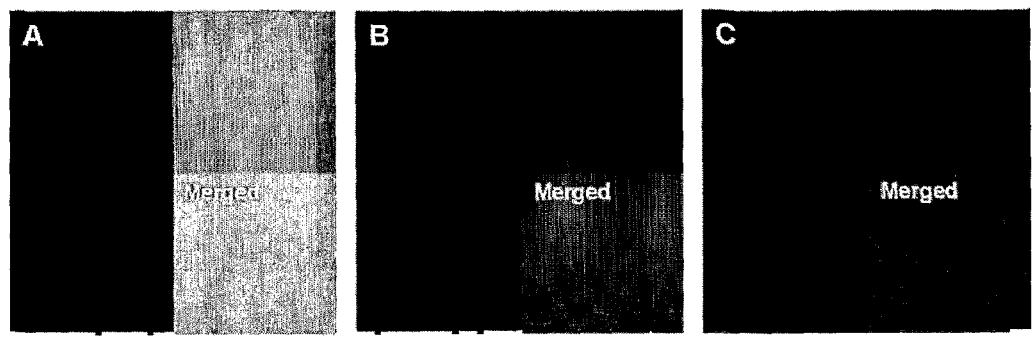
FIG. 12: Confocal images show a coated A-B-C surface with different ratios of rGFP, rBFP, and rCherry. (A) ratio of 3:2:1, (B) ratio of 2:2:2, (C) ratio of 1:2:3 of rGFP:rBFP:rCherry.

The A-B-C block copolymer system was prepared as in Example 2. Surfaces were then functionalised with three recombinant fluorescent proteins; Green fluorescent protein (GFP), Blue fluorescent protein (BFP) and Cherry. These were linked to the surface using the zinc linker strategy. They were linked in various ratios of 4:2:0, 3:2:1, 2:2:2, 1:2:3, 0:2:4 of 40 μg/ml GFP:BFP:Cherry and the amount of fluorescence was measured using confocal microscopy (FIG. 12). This example demonstrates the ability to control the binding of three separate proteins to the surface by controlling their concentration in the binding solution.

Figure 13:
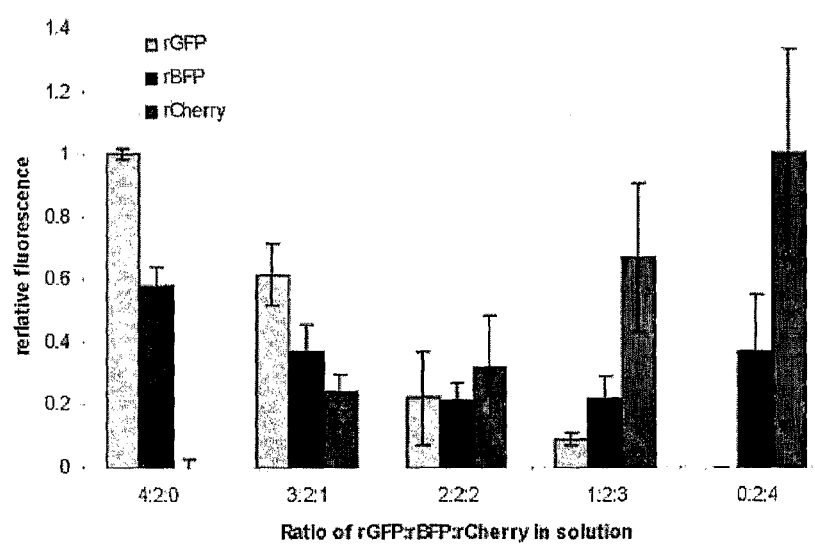
FIG. 13: The data shows that the binding of multiple proteins to the surface can be controlled by the ratio of the proteins in solution. Each point is the mean relative fluorescence±SD for N=6 replicates. rGFP is left-most, rBFP is central, and rCherry is right-most for each x data point.

The data also shows that the addition of a mix of the 3 proteins during the binding process presents a combination of the 3 proteins on the surface that is correlated with the ratio in which they were added (FIG. 13).

Example 7

Adhesion of hES Cells to Surface of Polymer of Example 2 Functionalised with Various Proteins/Peptides The A-B-C block copolymer system was prepared as in Example 2. Surfaces were then functionalised with 1) full-length proteins; fibronectin (Fn), 2) recombinant proteins; recombinant Fn, recombinant vitronectin (rVn), and 3) short peptides; RGD, RGE. Full length proteins and short peptides were covalently linked to the surface directly, while the recombinant proteins were linked either covalently or via the zinc-linker peptide intermediate.

Figure 14:
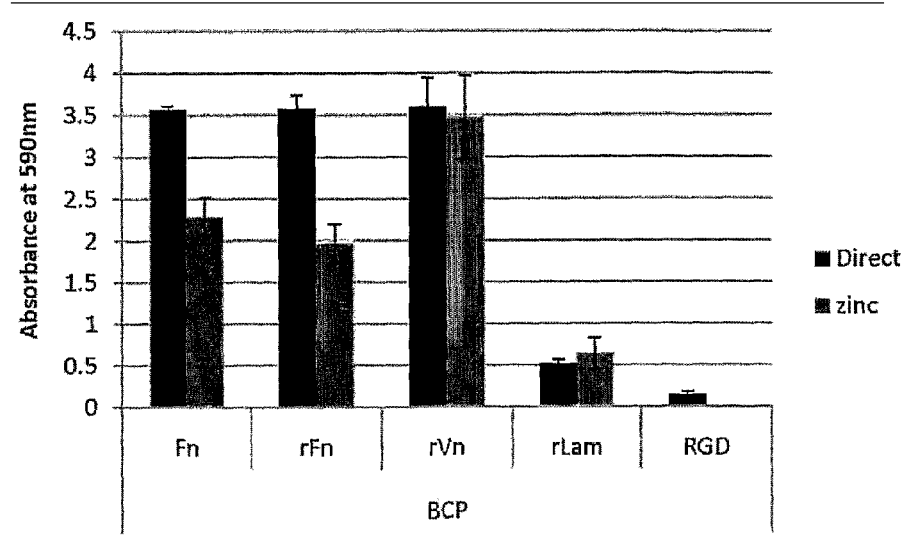
FIG. 14: Crystal violet binding assay to quantify the relative number of MEL2 hES cells binding to a peptide-functionalised surface. The peptides or proteins were linked to the surface either directly or via the zinc-linker peptide.
Figure 15:
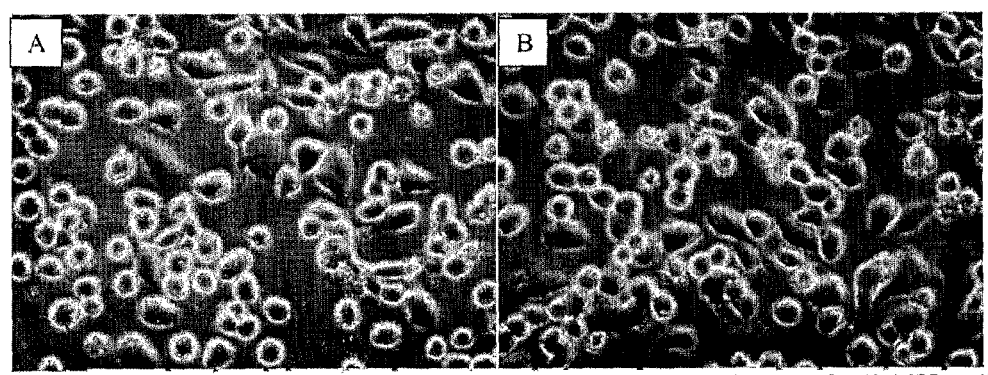
FIG. 15: Mel2 hES cell attachment (2 hours incubation) (a) Mel2 hES cells binding to rFn surface. (b) Mel2 hES cells binding to rVn surface.

The adhesion of hES cells to these functionalised surfaces was assessed (FIGS. 14 and 15).

Example 8

Adhesion of MSC to Surface of Polymer of Example 2

The A-B-C block copolymer system was prepared as in Example 2. Surfaces were then functionalised with RGD or RGE.

Figure 16:
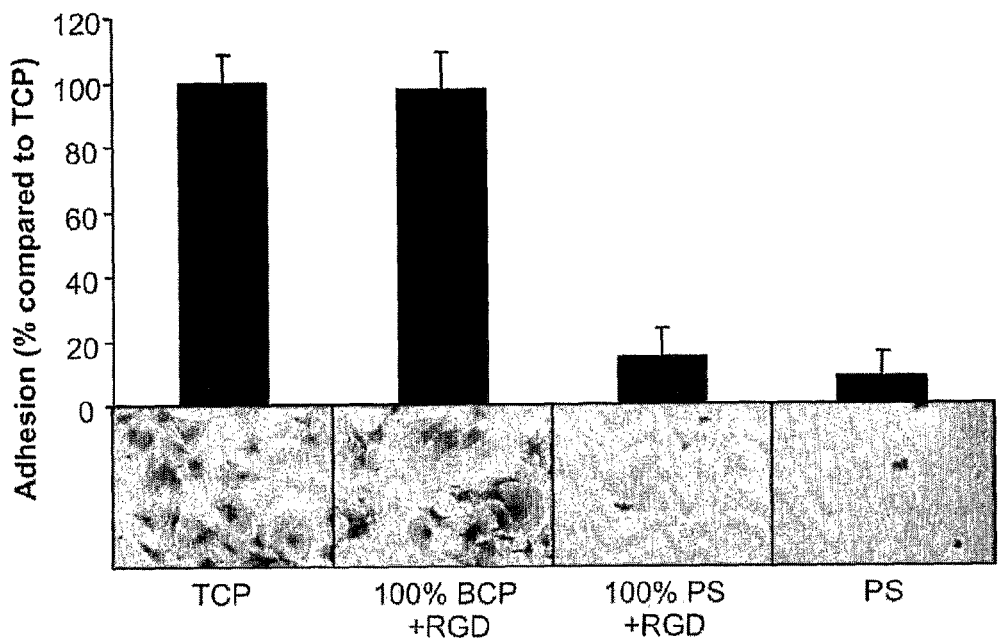
FIG. 16: Comparison of MSC binding to TCP, functionalised surface and control surfaces.

Adhesion assays were performed to determine the specificity of MSC adhesion to these functionalized surfaces (FIG. 16). MSCs adhered to RGD-functionalised 100% A-B-C surfaces at a level equivalent to tissue culture plastic (TCP). There was no binding of MSCs to polystyrene (PS) surfaces or PS surfaces that had been exposed to RGD peptide.

Figure 17:
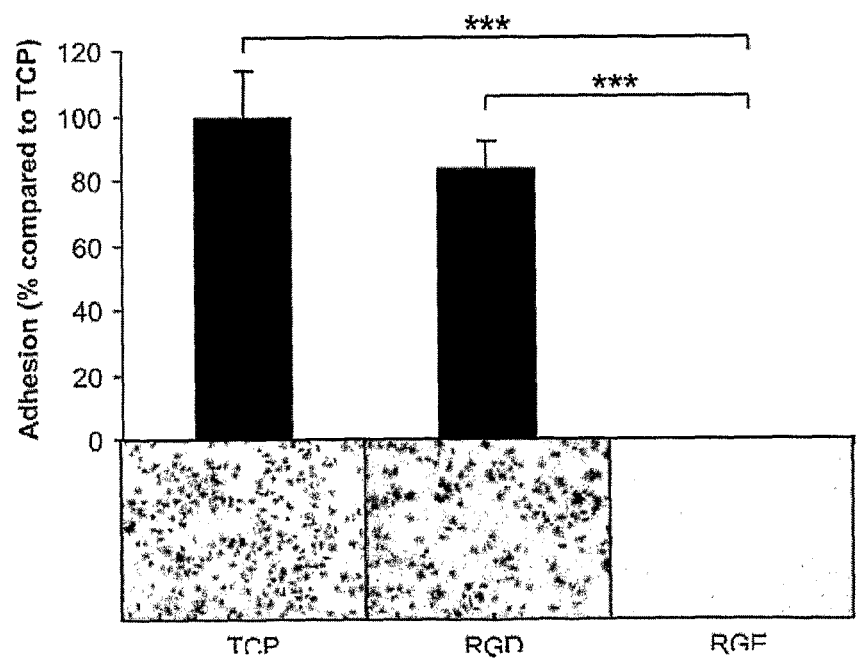
FIG. 17: Comparison of MSC binding to TCP and A-B-C surfaces functionalised with short peptides.

Adhesion assays were performed to determine the extent of MSC adhesion to 100% A-B-C surfaces (ie no PS surface polymer) functionalised with either RGD or RGE peptides and to tissue culture plastic (TCP) (FIG. 17). MSCs attached to the RGD-functionalised surface at a level similar to that of TCP. However, there was no attachment to the RGE peptide, confirming that adhesion was specific to the presented ligand and not background binding to the BCN surface.

Example 9

Importance of when the C Group of the Polymer of Example 2 is Functionalised

Figure 18:
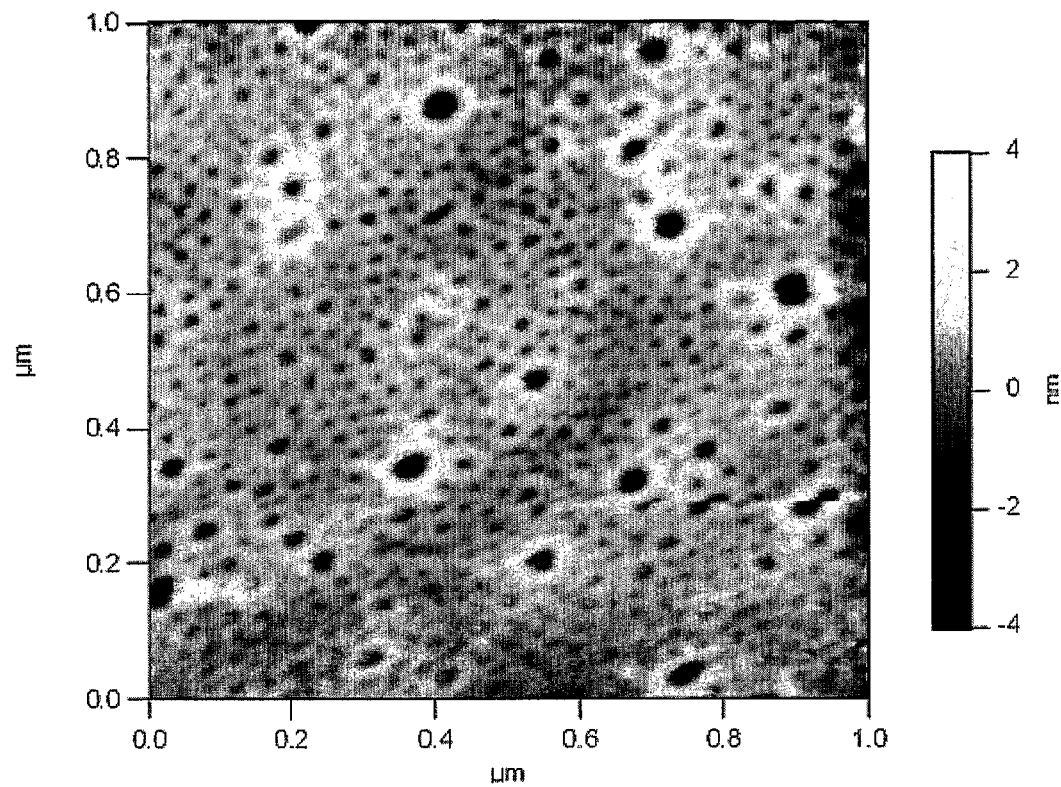
FIG. 18: AFM imaging of surface where the polymer had been functionalised prior to preparation of the surface. Note the presence of the characteristic nano-pattern.

An A-B-C block copolymer system as in Example 2 was prepared in 2 ways. In the first, the surface was prepared as in Example 2 and then subsequently functionalised with a short peptide (RGD) via the C group. In the second, C was used to attach the short peptide to the A-B polymer and then the surface was prepared. The preparation route was shown to not noticeably affect the resultant nano-pattern (FIG. 18).

Figure 19:
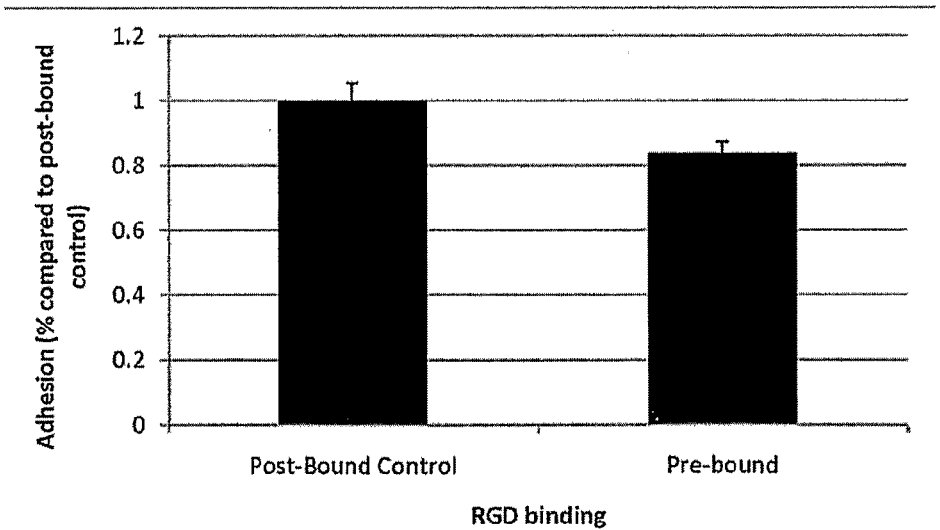
FIG. 19: Comparison of MSC cell adhesion to surfaces with peptide bound both before and after surface preparation.

MSC cells were incubated with the surfaces pre-bound with the RGD, and the surfaces performed similarly to those post-bound with the same peptide (FIG. 19).

Example 10

Blocking of Integrin Mediated Cell Adhesion on Surface of Polymer of Example 2 Functionalised with RGD The A-B-C block copolymer system was prepared as in Example 2. Surfaces were then functionalised with RGD.

Figure 20:
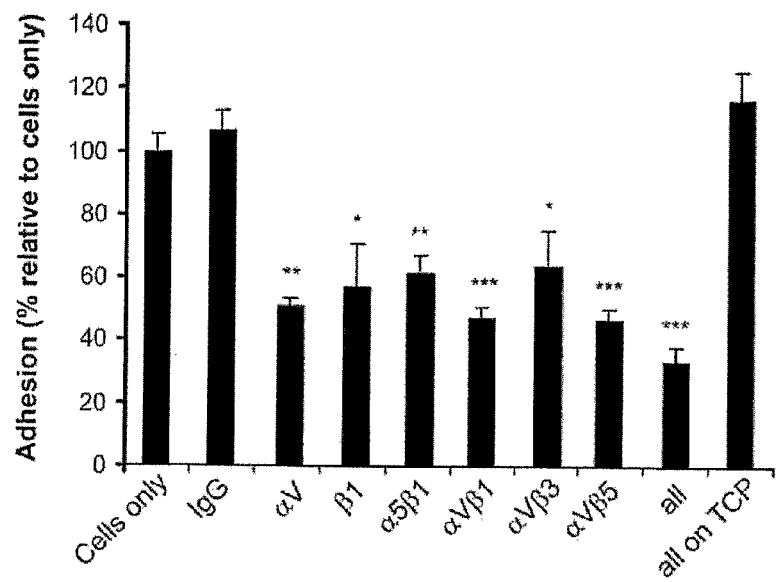
FIG. 20: Integrins involved in the binding of the MSCs to the RGD peptide.

Adhesion assays on RGD-functionalised 100% A-B-C surfaces in which the MSCs had been previously incubated with integrin blocking antibodies showed that the adhesion was mediated by α5, αV, β1, β3, and β5 integrins (FIG. 20). The greatest inhibition was seen when MSCs were blocked with a combination of all of these antibodies. However, there was no effect of the antibodies on adhesion of MSCs to TCP.

Example 11

MSC Morphology, and Effect of Inter-Domain Spacing Thereon, on Surface of Polymer of Example 2 Functionalised with RGD The A-B-C block copolymer system was prepared as in Example 2. Surfaces were then functionalised with RGD.

Figure 21:
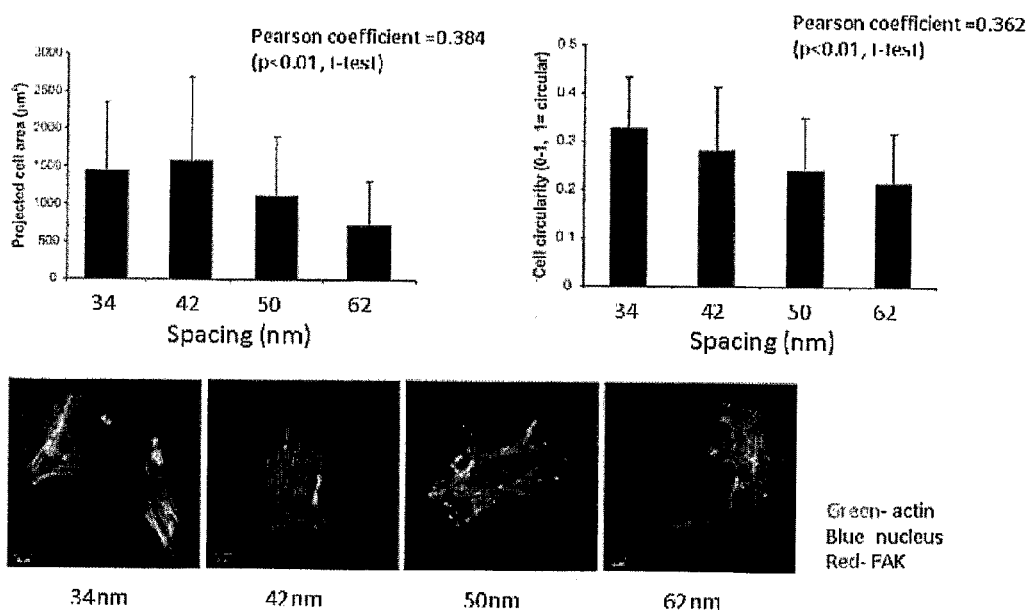
FIG. 21: Comparison of cell morphology when adhered to functionalised A-B-C with different pattern spacing.

The morphology of MSCs plated onto different ratios of PS-PEO-maleimide/PS was assessed. As the proportion of block co-polymer decreases the distance between the nano-islands increases. Both the projected cell area and cell circularity decreased as the distance between the RGD peptides increased (FIG. 21). These had Pearson coefficients of 0.384 and 0.362 respectively (p<0.01, t-test). The decrease in cell circularity is indicative of the increased number of protrusions visible in many of the MSCs on surfaces with increased lateral spacing of RGD peptide. Confocal analysis of cytoskeletal morphology showed that MSCs cultured on surfaces of 100 and 75% A-B-C had defined stress fibres. However, on 50% and 25% A-B-C surfaces, although some of the MSCs could still form stress fibres, many of the cells had an irregular shape with a large number of filopodia and a disorganised actin cytoskeleton. There was also a decrease in the amount of focal adhesion kinase (FAK) produced by MSCs on surfaces with increased RGD spacing.

Figure 22:
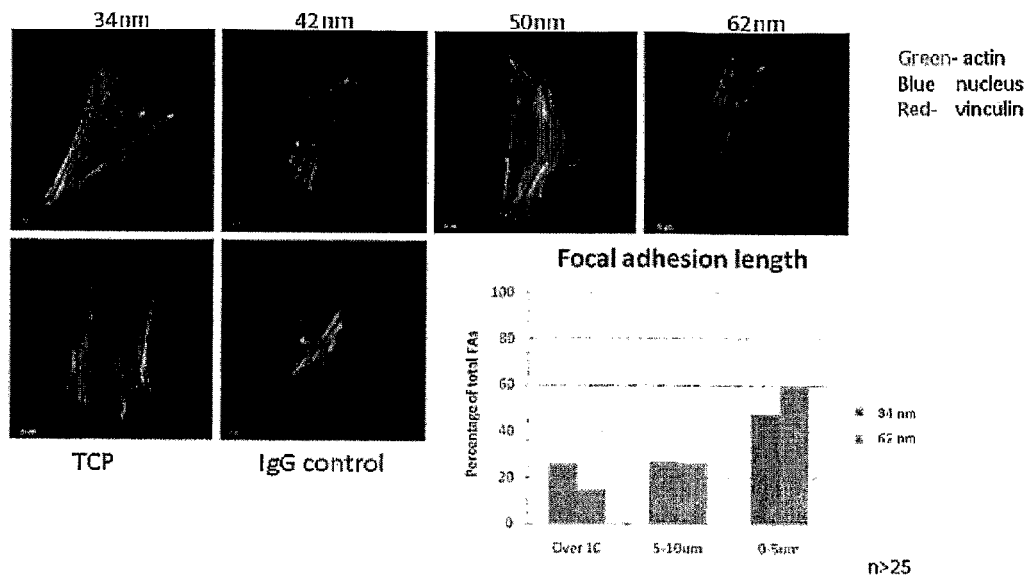
FIG. 22: Analysis of focal adhesion length within MSCs adhered to functionalised A-B-C with different pattern spacing.

Vinculin staining was used to assess the development of focal adhesions in MSCs cultured on different A-B-C/PS ratios. MSCs cultured on 100% A-B-C surfaces (34 nm spacing) had many large areas of vinculin staining indicative of mature focal adhesions (FIG. 22). As the percentage of block copolymer decreased (and spacing increased), this staining decreased with MSCs on 25% A-B-C surfaces (62 nm spacing) showing only a diffuse pattern of vinculin staining across the cell surface which is consistent with a reduced ability to form mature focal adhesions. Image analysis was used to quantify this change and showed that MSCs on 100% A-B-C had more of the mature fibrillar adhesion over 10 um in length whilst MSCs cultured on 25% A-B-C surfaces had more adhesions of 0-5 um in length, characteristic of nascent adhesion complexes. These differences in complex formation will have consequences for intracellular signalling.

Example 12

Cell Motility, and Effect of Inter-Domain Spacing Thereon, on Surface of Polymer of Example 2 Functionalised with RGD The A-B-C block copolymer system was prepared as in Example 2. Surfaces were then functionalised with RGD.

Figure 23:
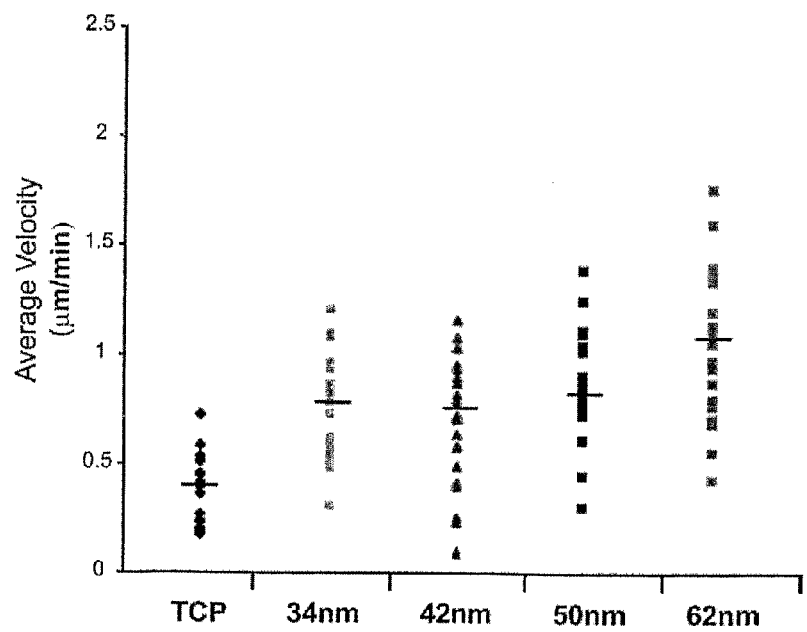
FIG. 23: Differences in cell velocity when plated on nano-islands with increasing spacing.

The motility of MSCs settling onto the surfaces was assessed and the average velocity over a 4 hr period determined. The average velocity was significantly higher in MSCs on the 25% A-B-C surface (62 nm) than on surfaces composed of 100, 75 and 50% A-B-C (34, 42 and 50 nm spacing) or MSCs on TCP (FIG. 23). This may have potential consequences for the ability of MSCs to migrate through and colonise a scaffold.

Example 13

Differentiation Markers in MSCs Cultures, and Effect of Inter-Domain Spacing Thereon, on Surface of Polymer of Example 2 Functionalised with RGD The A-B-C block copolymer system was prepared as in Example 2. Surfaces were then functionalised with RGD.

Figure 24:
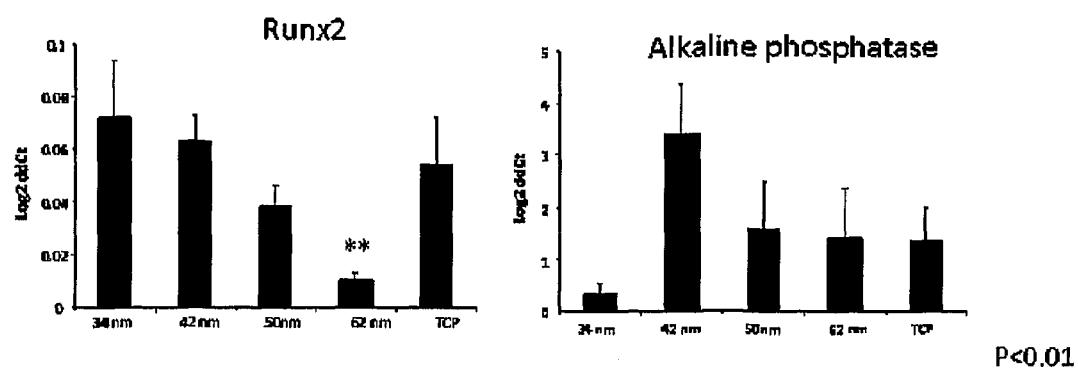
FIG. 24: qPCR analysis of osteogenic markers from MSCs grown on A-B-C/PS surfaces.

The ability of MSCs to undergo osteogenic differentiation on different surfaces was assessed using qPCR to determine the relative expression levels of the osteogenic markers Runx2 and alkaline phosphatase after 7 days of differentiation (FIG. 24). The levels of the transcription factor Runx2 decreased as the percentage of A-B-C decreased (and ligand spacing increased). Alkaline phosphatase levels were stable except for an increase in MSCs cultured on the 75% A-B-C surface (42 nm spacing).

Figure 25:
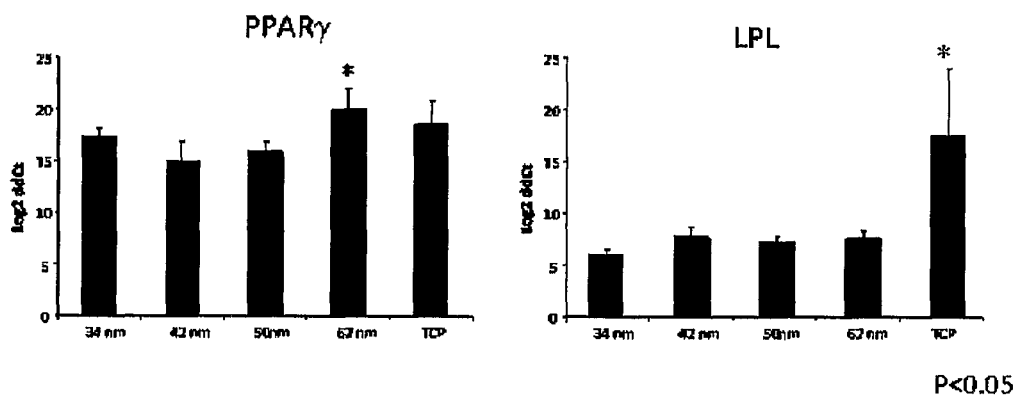
FIG. 25: qPCR analysis of adipogenic markers from MSCs grown on A-B-C/PS surfaces.

The ability of MSCs to undergo adipogenic differentiation on different surfaces was assessed using qPCR to determine the relative expression levels of the adipogenic markers PPARg and LPL after 7 days of differentiation (FIG. 25). There were no significant changes in LPL expression but there was significantly higher expression of PPARg in MSCs cultured in the 25% A-B-C surface (62 nm).

Example 14

Production of Microsphere of Polymer of Example 2

Figure 26:
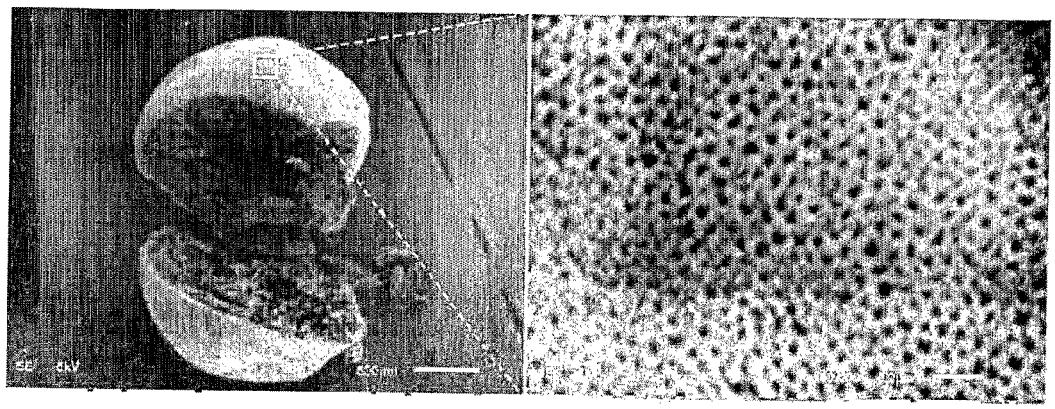
FIG. 26. SEM micrographs of A-B-C microsphere manufactured from dimethyl carbonate solution. Left shows the inner microstructure of the porous microspheres. Right shows high resolution SEM micrograph showing the nano-pattern structure of the A-B-C microsphere.

Highly porous inter-connected A-B-C microsphere was generated by temperature induced phase separation of a polymer-solvent solution. 5% (w/v) fraction solution of polymer in dimethyl carbonate was poured into controlled temperature water at 7° C. The emulsion was stirred at 200 rpm and cooled from 7° C. to 3° C. at a rate of 0.5° C./min. The solution was then transferred to liquid nitrogen for 2 min to freeze the structure and freeze dried. The resulting microspheres were imaged using a SEM and the presence of the nano-pattern was confirmed (FIG. 26).

Example 15

Production of Ink Jet Printed Block Copolymer Surface of Example 2

Figure 27:
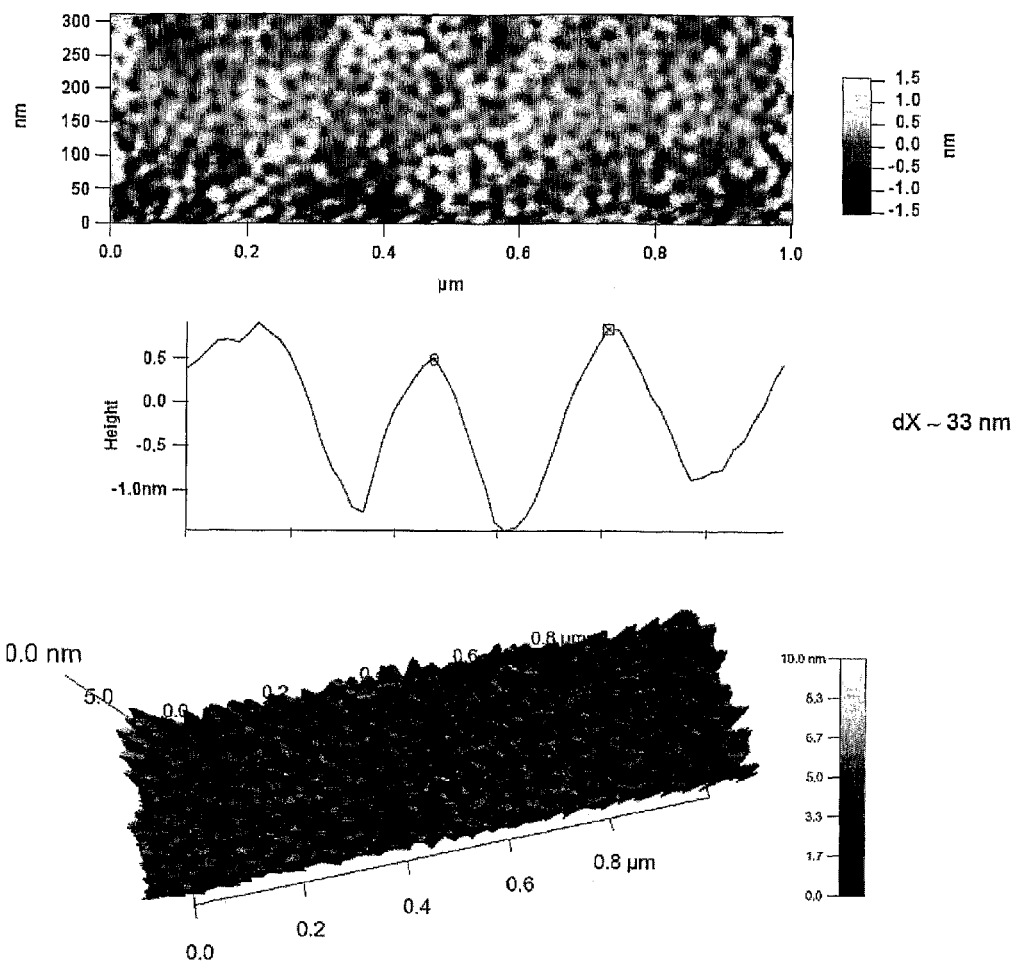
FIG. 27: AFM imaging of the internal region of an ink jet printed block copolymer surface (image from a representative single spot of 50 microns in diameter). Note the presence of the characteristic nano-pattern and the regularity (shown by the profile and 3D projection image).

1% (w/v) block copolymer solutions were prepared as in Example 2. These solutions were then ink jet printed (using a Litrex Ltd. Ink Jet Printer (Cambridge, U.K.)) through 10 micron diameter nozzles onto hydrophobised glass substrates to produce circular spots of approximately 50 microns in diameter (at a rate of approximately 3000 spots per second). The resulting spots were imaged using an AFM and the presence of the nano-pattern across the profile of the spots was confirmed (FIG. 27).

It will be understood that the invention disclosed and defined in this specification extends to all alternative combinations of two or more of the individual features mentioned or evident from the text or drawings. All of these different combinations constitute various alternative aspects of the invention.

The invention claimed is:

1. A polymer structure comprising a surface formed substantially from a surface polymer and being nano-patterned with a plurality of functionalised surface domains extending from or formed in the surface of the surface polymer, the functionalised surface domains being formed by solidifying a block copolymer of the general formulae A-B-C, wherein A is a polymer which is the same as the surface polymer or fully miscible or partially immiscible with or substantially miscible in the surface polymer;

B is a polymer which is more immiscible in the surface polymer than polymer A; and C is a terminal group; and wherein the surface domain includes the B block and the C group, with the A block being substantially embedded in the surface polymer and the C group includes a moiety selected from the group consisting of (male)imides, —COOH, —SH, —SO$_4^{2-}$, PO$_4^{3-}$, —NH$_3$, -vinyl sulphone, -epoxy, -alkyne, -hydrazide, -aldehyde, —C(CH$_3$)$_3$, —C$_6$F$_5$, cell binding domains from extracellular matrix molecules, a small molecule or moiety that has biofunctionality and a small molecule or moiety that can interact with other molecules that have biofunctionality.

2. The structure of claim 1, wherein the surface polymer is a homopolymer.

3. The structure of claim 1, wherein the surface domain is from about 10 nm to about 100 nm.

4. The structure of claim 1, wherein the C group is a terminal portion of the B block.

5. The structure of claim 1, wherein the C group is a cell binding domain of an extracellular matrix molecule selected from the group consisting of laminin, fibronectin, vitronectin and collagen.

6. The structure of claim 1, wherein the amount of block copolymer in surface polymer is more than about 0.5 parts per million.

7. The structure of claim 1, wherein the surface polymer is a block copolymer.

8. The structure of claim 1, wherein a biomolecule is attached to the C block.

9. The structure of claim 1, wherein the structure is a coating, film or surface applied to the surface of an existing substrate or support.

10. The structure of claim 9, wherein the existing substrate or support is an artificial cell culture system.

11. The structure of claim 1, wherein the existing substrate or support is a bioassay system.

12. The structure of claim 1, wherein the coating thickness is greater than about 25 nm.

13. The structure of claim 1, wherein the C group does not substantially affect the miscibility of the B block in the A block or in the surface polymer.

* * * * *